United States Patent
Uchida et al.

(10) Patent No.: US 12,397,054 B2
(45) Date of Patent: Aug. 26, 2025

(54) ANTIBODY CAPABLE OF INDUCING IMMUNE TOLERANCE PRODUCED USING CELL MIXTURE HAVING COMPLEXED STATE, AND INDUCED LYMPHOCYTE OR CELL THERAPEUTIC AGENT AND CELL THERAPY METHOD EACH USING INDUCED LYMPHOCYTE

(71) Applicant: JUNTEN BIO Co., Ltd., Tokyo (JP)

(72) Inventors: Koichiro Uchida, Tokyo (JP); Kazuyoshi Takeda, Tokyo (JP); Ko Okumura, Tokyo (JP)

(73) Assignee: JUNTEN BIO Co., Ltd., Tokyo (JP)

( * ) Notice: Subject to any disclaimer, the term of this patent is extended or adjusted under 35 U.S.C. 154(b) by 1089 days.

(21) Appl. No.: 17/254,094

(22) PCT Filed: Jun. 21, 2019

(86) PCT No.: PCT/JP2019/024753
§ 371 (c)(1),
(2) Date: Dec. 18, 2020

(87) PCT Pub. No.: WO2019/245038
PCT Pub. Date: Dec. 26, 2019

(65) Prior Publication Data
US 2021/0260124 A1 Aug. 26, 2021

(30) Foreign Application Priority Data
Jun. 22, 2018 (JP) ................ 2018-119001

(51) Int. Cl.
*A61K 40/41* (2025.01)
*A61K 40/10* (2025.01)
(Continued)

(52) U.S. Cl.
CPC ............ *A61K 40/418* (2025.01); *A61K 40/10* (2025.01); *A61K 40/11* (2025.01); *A61K 40/22* (2025.01);
(Continued)

(58) Field of Classification Search
CPC ...... A61K 35/17; A61K 39/001; A61K 39/35; A61K 39/461; A61K 39/4611;
(Continued)

(56) References Cited

FOREIGN PATENT DOCUMENTS

| JP | 2002-504120 A | 2/2002 |
|----|---------------|--------|
| JP | 2003-33175 A | 2/2003 |

(Continued)

OTHER PUBLICATIONS

Davies, Jeffrey K. "Costimulatory blockade with monoclonal antibodies to induce alloanergy in donor lymphocytes." International journal of hematology 93.5 (2011): 594-601 (Year: 2011).*

(Continued)

*Primary Examiner* — Tracy Vivlemore
*Assistant Examiner* — Thomas R. Amick
(74) *Attorney, Agent, or Firm* — Seed IP Law Group LLP

(57) ABSTRACT

The present disclosure provides a pharmaceutical composition for antigen-specific immune tolerance or immune present suppression. The disclosure provides pharmaceutical composition comprising a CD4-positive anergy T cell and a CD8-positive anergy T cell. In some embodiments, the anergy T cell is induced by an antibody capable of inhibiting the interaction between CD80 and/or CD86 and CD28. In a specific embodiment, the pharmaceutical composition May additionally comprise a regulatory T cell (e.g., a FOXP3-positive CD4-positive CD25-positive T cell).

12 Claims, 6 Drawing Sheets

(51) Int. Cl.
*A61K 40/11* (2025.01)
*A61K 40/22* (2025.01)
*A61K 40/42* (2025.01)
*A61P 37/06* (2006.01)
*C12N 5/0783* (2010.01)

(52) U.S. Cl.
CPC .......... *A61K 40/4211* (2025.01); *A61P 37/06* (2018.01); *C12N 5/0637* (2013.01)

(58) Field of Classification Search
CPC .......... A61K 39/4621; A61K 39/46434; A61K 39/464412; A61K 2039/505; A61K 2039/577; A61P 37/06; A61P 37/08; C07K 2317/76; C07K 16/2827; C07K 16/18; C07K 16/2812; C07K 16/2815; C12N 2501/51; C12N 5/0637; C12Q 1/6804

See application file for complete search history.

(56) References Cited

FOREIGN PATENT DOCUMENTS

| | | | |
|---|---|---|---|
| JP | 2005-530762 A | 10/2005 | |
| JP | 2007-131598 A | 5/2007 | |
| JP | 2011-500730 A | 1/2011 | |
| JP | 2011-502163 A | 1/2011 | |
| JP | 2016-520081 A | 7/2016 | |
| KR | 10-2013-0049775 A | 5/2013 | |
| WO | 98/56417 A1 | 12/1998 | |
| WO | 03/094840 A2 | 11/2003 | |
| WO | 2009/052623 A1 | 4/2009 | |
| WO | 2009/058888 A1 | 5/2009 | |
| WO | 2011/113019 A2 | 9/2011 | |
| WO | 2014/186193 A1 | 11/2014 | |

OTHER PUBLICATIONS

Cutolo, Maurizio et al. "CTLA4-Ig interacts with cultured synovial macrophages from rheumatoid arthritis patients and downregulates cytokine production." Arthritis research & therapy vol. 11,6 (Year: 2009).*

Schumann, Julia et al. "Differences in CD44 Surface Expression Levels and Function Discriminates IL-17 and IFN-γ Producing Helper T Cells." PloS one vol. 10,7 e0132479. Jul. 14, 2015 (Year: 2015).*

Topham, David J, and Emma C Reilly. "Tissue-Resident Memory CD8+ T Cells: From Phenotype to Function." Frontiers in immunology vol. 9 515. Mar. 26, 2018 (Year: 2018).*

Waller, Edmund K., et al. "Facilitating T-cell immune reconstitution after haploidentical transplantation in adults." Blood Cells, Molecules, and Diseases 33.3 (2004): 233-237 (Year: 2004).*

Bashuda, "Immune tolerance in kidney transplantation Immune animals (monkeys), transplant," *Special Issue: Cutting Edge of Immune Tolerance Immune Tolerance in Kidney Transplantation-Medium Sized Animals (Monkeys)* 41(2):83-87, 2006 (w/English translation), 17 pages.

Bashuda et al., "Renal allograft rejection is prevented by adoptive transfer of anergic T cells in nonhuman primates," *J. Clin. Invest.* 115:1896-1902, 2005.

Davies et al., "Induction of Alloanergy in Human Donor T Cells Without Loss of Pathogen or Tumor Immunity," *Transplantation* 86:854-864, 2008.

Mori et al., "T cell anergy and immunotherapy," Molecular Biology of Allergy 2 170(12):993-997, 1994, (w/English translation), 17 pages.

Pacciani et al., "Induction of anergic allergen-specific suppressor T cells using tolerogenic dendritic cells derived from children with allergies to house dust mites," *J Allergy Clin Immunol* 125:727-736, 2010.

Steinbrink et al., "$CD4^+$ and $CD8^+$ anergic T cells induced by interleukin-10-treated human dendritic cells display antigen-specific suppressor activity," *Blood* 99:2468-2476, 2002.

Teraoka et al., "A Clinical Trial Aiming at Tolerance Induction by Adoptive Transfer of Ex Vivo-Induced, Donor-Specific Treg-Like Cells in Clinical Kidney Transplantation," *J Transplant Res* 2(1): doi http://dx.doi.org/10.16966/2473-1730.115, 2017, 8 pages.

Todo et al., "A Pilot Study of Operational Tolerance With a Regulatory T-Cell-Based Cell Therapy in Living Donor Liver Transplantation," *Hepatology* 64(2):632-643, 2016.

Kalekar et al., "Relationship between CD4 Regulatory T Cells and Anergy In Vivo," *J Immunol* 198(7): 2527-2533, Apr. 1, 2017. (7 pages).

* cited by examiner

ANTIBODY CAPABLE OF INDUCING IMMUNE TOLERANCE PRODUCED USING CELL MIXTURE HAVING COMPLEXED STATE, AND INDUCED LYMPHOCYTE OR CELL THERAPEUTIC AGENT AND CELL THERAPY METHOD EACH USING INDUCED LYMPHOCYTE

TECHNICAL FIELD

The present disclosure relates to a novel technology related to immune tolerance. More specifically, the present disclosure relates to a pharmaceutical composition comprising an anergic T cell, manufacture of the pharmaceutical composition, and quality control for the pharmaceutical composition.

BACKGROUND ART

Liver transplantation has been widely used as the final treatment on terminal liver failure patients. 20,000 or more liver transplantations are performed abroad, and more than 500 are performed in Japan annually.

Transplantation is one of the major treatments chosen for terminal organ failure of the kidney, heart, liver, or pancreas. Despite the dramatic advancement in the treatment of graft rejection in recent years, the majority of transplantations are ultimately rejected without any immunosuppressive regimen. Today's drug immunosuppressive regimen which is dependent on continuous drug therapy suppresses not only responses that are clearly directed to transplantation, but also all immune responses, such that organ transplant patients become more vulnerable to increased sensitivity to infections and cancer.

While regenerative medicine has also drawn attention, immune rejection can ultimately occur without any autologous cells even if induced pluripotent stem cells (iPS cells) or the like are used. Thus, immune tolerance technologies have garnered attention.

Such technologies for inducing immune tolerance include induction of an antigen specific non-immune response (anergy) of T cells. Specific technologies reported include a technology for directly administering an antibody which inhibits interactions between CD80/CD86 on antigen presenting cells and CD28 on unactivated (naïve) T cells to an organ transplant patient to induce donor antigen specific anergy in the body (Patent Literature 1) and a technology of co-culturing recipient cells and radiation irradiated donor cells in the presence of the same antibody to induce donor antigen specific anergic cells ex vivo and returning said cells to the recipient (Patent Literature 2, Patent Literature 3, and Non Patent Literatures 1 to 3).

Non Patent Literature 1 reports that removal of CD8 positive cells hardly has any effect on immunosuppression in the technology of inducing a donor antigen specific anergic cell ex vivo and returning the cell to a recipient.

CITATION LIST

Patent Literature

[PTL 1] Japanese National Phase PCT Laid-open Publication No. 2002-504120
[PTL 2] Japanese National Phase PCT Laid-open Publication No. 2007-131598
[PTL 3] Japanese National Phase PCT Laid-open Publication No. 2016-520081

Non Patent Literature

[NPL 1] Satoru Todo et al. Hepatorogy, 64 (vol. 2), 632-643 (2016)
[NPL 2] Teraoka S, Koyama I, Bashuda H, Uchida K, Tonsho M, et al. (2017) J Transplant Res 2 (1) p 1-8
[NPL 3] Bashuda H et al., J. Clin. Invest. 115:1896-1902 (2005).

SUMMARY OF INVENTION

Solution to Problem

The inventors found for the first time that even if anergy of T cells is induced using an inhibitory factor such as an antibody inhibiting the interaction between CD80/CD86 and CD28, the ability to induce immune tolerance decreases significantly in cases without a CD8 positive cell in a mixture of anergy induced T cells as compared to cases with a CD8 positive cell. The inventors found that CD8 positive cells play a critical role in the induction of immune tolerance.

Therefore, the present disclosure provides the following.
(1) A pharmaceutical composition comprising a CD4 positive anergic T cell and a CD8 positive anergic T cell.
(2) The pharmaceutical composition of the preceding item, wherein the anergic T cell is induced by an inhibitory factor that can inhibit an interaction between CD80 and/or CD86 and CD28.
(3) The pharmaceutical composition of any of the preceding items, wherein the inhibitory factor is selected from the group consisting of a small molecule, a protein, a nucleic acid, a lipid, a saccharide, and a combination thereof.
(4) The pharmaceutical composition of any of the preceding items, wherein the protein is an antibody or a variant thereof, or a cell surface molecule or a variant thereof.
(5) The pharmaceutical composition of any of the preceding items, wherein the variant of the antibody is an antigen binding fragment.
(6) The pharmaceutical composition of any of the preceding items, wherein the variant of the cell surface molecule is a fusion protein.
(7) The pharmaceutical composition of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.
(8) The pharmaceutical composition of any of the preceding items, wherein the CTLA4-Ig fusion protein is abatacept or belatacept.
(9) The pharmaceutical composition of any one of items 1 to 8, further comprising a regulatory T cell.
(10) The pharmaceutical composition of any of the preceding items, wherein the regulatory T cell is FOXP3 positive CD4 positive CD25 positive.
(11) A pharmaceutical composition comprising a cell having anergy induced by an inhibitory factor that can inhibit an interaction between CD80 and/or CD86 and CD28, wherein the composition comprises a CD8 positive cell, and the composition further comprises at least one of a FOXP3 positive cell and a CD4 positive cell.

(12) The pharmaceutical composition of any of the preceding items, comprising all of a FOXP3 positive cell, a CD4 positive cell, and a CD8 positive cell.
(13) The pharmaceutical composition of any of the preceding items, wherein the CD8 positive cell is CD44 positive.
(14) The pharmaceutical composition of any of the preceding items, wherein the CD8 positive cell is CD45RA negative and CD45RO positive.
(15) The pharmaceutical composition of any of the preceding items, wherein the FOXP3 positive cell is CD4 positive.
(16) The pharmaceutical composition of any of the preceding items, wherein the FOXP3 positive cell is CD25 positive.
(17) The pharmaceutical composition of any of the preceding items, wherein the pharmaceutical composition is for antigen specific immune tolerance or immunosuppression.
(18) The pharmaceutical composition of any of the preceding items, wherein the antibody comprises an anti-CD80 antibody, an anti-CD86 antibody, a bispecific antibody to CD80 and CD86, an anti-CD28 antibody, or a combination thereof.
(19) The pharmaceutical composition of any of the preceding items, wherein the cell is a cell induced by a step of mixing the inhibitory factor, a cell derived from a subject, and an antigen derived from the subject or an antigen that is not derived from the subject or a material containing the antigen.
(20) A pharmaceutical composition for treating or preventing a disease, disorder, or condition in a subject caused by an antigen derived from the subject or an antigen that is not derived from the subject, comprising the composition of any of the preceding items.
(21) The pharmaceutical composition of any of the preceding items, wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.
(22) The pharmaceutical composition of any of the preceding items, wherein the graft rejection is caused by transplanting a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.
(23) The pharmaceutical composition of any of the preceding items, wherein the material containing the antigen is a cell.
(24) A method of manufacturing a medicament comprising a cell, the method comprising:
(A) mixing an inhibitory factor that can inhibit an interaction between CD80 and/or CD86 and CD28, a cell derived from a subject, and an antigen derived from the subject or an antigen that is not derived from the subject or a material containing the antigen;
(B) confirming that a cellular product obtained by the mixing comprises a CD8 positive cell; and
(C) confirming that the cellular product comprises at least one of a FOXP3 positive cell and a CD4 positive cell.
(25) The method of any of the preceding items, wherein the inhibitory factor is selected from the group consisting of a small molecule, a protein, a nucleic acid, a lipid, a saccharide, and a combination thereof.
(26) The method of any of the preceding items, wherein the protein is an antibody or a variant thereof, or a cell surface molecule or a variant thereof.
(27) The method of any of the preceding items, wherein the variant of the antibody is an antigen binding fragment.
(28) The method of any of the preceding items, wherein the variant of the cell surface molecule is a fusion protein.
(29) The method of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.
(30) The method of any of the preceding items, wherein the CTLA4-Ig fusion protein is abatacept or belatacept.
(31) The method of any of the preceding items, wherein the presence of a CD8 positive cell and the presence of at least one of a FOXP3 positive cell and a CD4 positive cell in the cellular product indicate that the cellular product can be used as a medicament.
(32) The method of any of the preceding items, wherein the medicament is for treating or preventing a disease, disorder, or condition in the subject caused by an antigen derived from the subject or an antigen that is not derived from the subject.
(33) The method of any of the preceding items, wherein step (B) comprises detecting CD8 with an anti-CD8 antibody, and step (C) comprises detecting at least one of FOXP3 and CD4 with at least one of an anti-FOXP3 antibody and an anti-CD4 antibody.
(34) The method of any of the preceding items, wherein the detection is performed by FACS.
(35) A method of controlling quality of a medicament comprising a cell for treating or preventing a disease, disorder, or condition in a subject caused by an antigen expressed in a cell derived from the subject or an antigen that is not derived from the subject, the method comprising: (A) confirming that the cell comprises a CD8 positive cell; and (B) confirming that the cell comprises at least one of a FOXP3 positive cell and a CD4 positive cell.
(36) The method of any of the preceding items, wherein step (A) comprises detecting CD8 with an anti-CD8 antibody, and step (B) comprises detecting at least one of FOXP3 and CD4 with at least one of an anti-FOXP3 antibody and an anti-CD4 antibody.
(37) The method of any of the preceding items, wherein the detection is performed by FACS, Western blot, or PCR.
(38) A composition comprising an inhibitory factor for the manufacture of the pharmaceutical composition of any of the preceding items, wherein the inhibitory factor is an inhibitory factor that can inhibit an interaction between CD80 and/or CD86 and CD28.
(39) The composition of any of the preceding items, wherein the inhibitory factor is selected from the group consisting of a small molecule, a protein, a nucleic acid, a lipid, a saccharide, and a combination thereof.
(40) The composition of any of the preceding items, wherein the protein is an antibody or a variant thereof, or a cell surface molecule or a variant thereof.
(41) The composition of any of the preceding items, wherein the variant of the antibody is an antigen binding fragment.

(42) The composition of any of the preceding items, wherein the variant of the cell surface molecule is a fusion protein.

(43) The composition of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.

(44) The composition of any of the preceding items, wherein the CTLA4-Ig fusion protein is abatacept or belatacept.

(45) A kit for manufacturing a medicament comprising a mixture of cells, the kit comprising: (A) an inhibitory factor that can inhibit an interaction between CD80 and/or CD86 and CD28; (B) means for detecting CD8; and (C) means for detecting at least one of FOXP3 and CD4.

(46) The kit of any one of the preceding items, wherein the inhibitory factor is selected from the group consisting of a small molecule, a protein, a nucleic acid, a lipid, a saccharide, and a combination thereof.

(47) The kit of any of the preceding items, wherein the protein is an antibody or a variant thereof, or a cell surface molecule or a variant thereof.

(48) The method of any of the preceding items, wherein the variant of the antibody is an antigen binding fragment.

(49) The method of any of the preceding items, wherein the variant of the cell surface molecule is a fusion protein.

(50) The kit or method of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.

(52) The kit or method of any of the preceding items, wherein the CTLA4-Ig fusion protein is abatacept or belatacept.

(53) The kit of any of the preceding items, wherein the presence of a CD8 positive cell and the presence of at least one of a FOXP3 positive cell and a CD4 positive cell in the mixture of cells indicate that the mixture of cells can be used as a medicament.

(54) The kit of any of the preceding items, wherein the medicament is for treating or preventing a disease, disorder, or condition in the subject caused by an antigen derived from the subject or an antigen that is not derived from the subject.

(55) A kit for controlling quality of a medicament comprising a cell for treating or preventing a disease, disorder, or condition in a subject caused by an antigen expressed in a cell derived from the subject or an antigen that is not derived from the subject, the kit comprising (A) means for detecting CD8 and (B) means for detecting at least one of FOXP3 and CD4.

(56) The kit of any of the preceding items, wherein the means for detecting CD8 comprises an anti-CD8 antibody, and the means for detecting at least one of FOXP3 and CD4 comprises at least one of an anti-FOXP3 antibody and an anti-CD4 antibody.

(57) The kit of any of the preceding items, wherein the detection is performed by FACS, Western blot, or PCR.

(B1)
A pharmaceutical composition comprising a CD8 positive anergic T cell, for eliciting immune tolerance from use with a CD4 positive anergic cell.

(B2)
The pharmaceutical composition of item B1, further comprising one or more features of any of items 1 to 57 or other items.

(C1)
A pharmaceutical composition comprising a CD4 positive anergic T cell, for eliciting immune tolerance from use with a CD8 positive anergic cell.

(C2)
The pharmaceutical composition of item B1, further comprising one or more features of any of items 1 to 57 or other items.

(D1)
A method of treating or preventing a disease, disorder, or condition in a subject caused by an antigen derived from the subject or an antigen that is not derived from the subject, comprising administering to the subject an effective amount of a CD4 positive anergic T cell and a CD8 positive anergic T cell.

(D2)
The method of the preceding item, wherein the anergic T cells is induced by an antibody that can inhibit an interaction between CD80 and/or CD86 and CD28.

(D3) The method of any of the preceding items, wherein the inhibitory factor is selected from the group consisting of a small molecule, a protein, a nucleic acid, a lipid, a saccharide, and a combination thereof.

(D4) The method of any of the preceding items, wherein the protein is an antibody or a variant thereof, or a cell surface molecule or a variant thereof.

(D5) The method of any of the preceding items, wherein the variant of the antibody is an antigen binding fragment.

(D6) The method of any of the preceding items, wherein the variant of the cell surface molecule is a fusion protein.

(D7) The method of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.

(D8) The method of any of the preceding items, wherein the CTLA4-Ig fusion protein is abatacept or belatacept.

(D9) The pharmaceutical composition of any one of items 1 to 8, further comprising administering a regulatory T cell.

(D10) The method of any of the preceding items, wherein the regulatory T cell is FOXP3 positive CD4 positive CD25 positive.

(D11) A method of treating or preventing a disease, disorder, or condition in a subject caused by an antigen derived from the subject or an antigen that is not derived from the subject, the method comprising administering to the subject an effective amount of a cell having anergy induced by an inhibitory factor that can inhibit an interaction between CD80 and/or CD86 and CD28, wherein the anergy induced cell comprises a CD8 positive cell, and wherein the anergy-induced cell comprises at least one of a FOXP3 positive cell and a CD4 positive cell.

(D12) The method of any of the preceding items, comprising all of a FOXP3 positive cell, a CD4 positive cell, and a CD8 positive cell.

(D13) The method of any of the preceding items, wherein the CD8 positive cell is CD44 positive.

(D14) The method of any of the preceding items, wherein the CD8 positive cell is CD45RA negative and CD45RO positive.

(D15) The method of any of the preceding items, wherein the FOXP3 positive cell is CD4 positive.

(D16) The method of any of the preceding items, wherein the FOXP3 positive cell is CD25 positive.

(D17) The method of any of the preceding items, wherein the anergy induced cell elicits antigen specific immune tolerance or immunosuppression.

(D18) The method of any of the preceding items, wherein the antibody comprises an anti-CD80 antibody, an anti-CD86 antibody, a bispecific antibody to CD80 and CD86, an anti-CD28 antibody, or a combination thereof.

(D19) The method of any of the preceding items, wherein the cell is a cell induced by a step of mixing the inhibitory factor, a cell derived from a subject, and an antigen derived from the subject or an antigen that is not derived from the subject or a material containing the antigen.

(D20) A method for treating or preventing a disease, disorder, or condition in a subject caused by an antigen derived from the subject or an antigen that is not derived from the subject, comprising the composition of any of the preceding items.

(D21) The method of any of the preceding items, wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.

(D22) The method of any of the preceding items, wherein the graft rejection is caused by transplanting a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.

(D23) The method of any of the preceding items, wherein the material containing the antigen is a cell.

(E1) Use of a CD4 positive anergic T cell and a CD8 positive anergic T cell, for the manufacture of a medicament for treating or preventing a disease, disorder, or condition in a subject caused by an antigen derived from the subject or an antigen that is not derived from the subject.

(E2) The use of the preceding item, wherein the anergic T cell is induced by an antibody that can inhibit an interaction between CD80 and/or CD86 and CD28.

(E3) The use of any of the preceding items, wherein the inhibitory factor is selected from the group consisting of a small molecule, a protein, a nucleic acid, a lipid, a saccharide, and a combination thereof.

(E4) The use of any of the preceding items, wherein the protein is an antibody or a variant thereof, or a cell surface molecule or a variant thereof.

(E5) The use of any of the preceding items, wherein the variant of the antibody is an antigen binding fragment.

(E6) The use of any of the preceding items, wherein the variant of the cell surface molecule is a fusion protein.

(E7) The use of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.

(E8) The use of any of the preceding items, wherein the CTLA4-Ig fusion protein is abatacept or belatacept.

(E9) The use of any one of items 1 to 8, wherein the CD4 positive anergic T cell and CD8 positive anergic T cell further comprise a regulatory T cell.

(E10) The use of any of the preceding items, wherein the regulatory T cell is FOXP3 positive CD4 positive CD25 positive.

(E11) Use of a cell having anergy induced by an inhibitory factor that can inhibit an interaction between CD80 and/or CD86 and CD28, for the manufacture of a medicament for treating or preventing a disease, disorder, or condition in a subject caused by an antigen derived from the subject or an antigen that is not derived from the subject, wherein the anergy induced cell comprises a CD8 positive cell, and the anergy induced cell comprises at least one of a FOXP3 positive cell and a CD4 positive cell.

(E12) The use of any of the preceding items, wherein the anergy induced cell comprises all of a FOXP3 positive cell, a CD4 positive cell, and a CD8 positive cell.

(E13) The use of any of the preceding items, wherein the CD8 positive cell is CD44 positive.

(E14) The use of any of the preceding items, wherein the CD8 positive cell is CD45RA negative and CD45RO positive.

(E15) The use of any of the preceding items, wherein the FOXP3 positive cell is CD4 positive.

(E16) The use of any of the preceding items, wherein the FOXP3 positive cell is CD25 positive.

(E17) The use of any of the preceding items, wherein the anergy induced cell elicits antigen specific immune tolerance or immunosuppression.

(E18) The use of any of the preceding items, wherein the antibody comprises an anti-CD80 antibody, an anti-CD86 antibody, a bispecific antibody to CD80 and CD86, an anti-CD28 antibody, or a combination thereof.

(E19) The use of any of the preceding items, wherein the anergy induced cell is a cell induced by a step of mixing the inhibitory factor, a cell derived from a subject, and an antigen derived from the subject or an antigen that is not derived from the subject or a material containing the antigen.

(E20) Use for treating or preventing a disease, disorder, or condition in a subject caused by an antigen derived from the subject or an antigen that is not derived from the subject, comprising the composition of any of the preceding items.

(E21) The use of any of the preceding items, wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.

(E22) The use of any of the preceding items, wherein the graft rejection is caused by transplanting a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.

(E23) The use of any of the preceding items, wherein the material containing the antigen is a cell.

(F1) A cell mixture of a CD4 positive anergic T cell and a CD8 positive anergic T cell for treating or preventing a disease, disorder, or condition in a subject caused by an antigen derived from the subject or an antigen that is not derived from the subject.

(F2) The cell mixture of the preceding item, wherein the anergic T cell is induced by an antibody that can inhibit an interaction between CD80 and/or CD86 and CD28.

(F3) The cell mixture of any of the preceding items, wherein the inhibitory factor is selected from the group consisting of a small molecule, a protein, a nucleic acid, a lipid, a saccharide, and a combination thereof.

(F4) The cell mixture of any of the preceding items, wherein the protein is an antibody or a variant thereof, or a cell surface molecule or a variant thereof.

(F5) The cell mixture of any of the preceding items, wherein the variant of the antibody is an antigen binding fragment.

(F6) The cell mixture of any of the preceding items, wherein the variant of the cell surface molecule is a fusion protein.

(F7) The cell mixture of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.

(F8) The cell mixture of any of the preceding items, wherein the CTLA4-Ig fusion protein is abatacept or belatacept.

(F9) The cell mixture of any one of items 1 to 8, further comprising a regulatory T cell.

(F10) The cell mixture of any of the preceding items, wherein the regulatory T cell is FOXP3 positive CD4 positive CD25 positive.

(F11) A cell having anergy induced by an inhibitory factor that can inhibit an interaction between CD80 and/or CD86 and CD28, for treating or preventing a disease, disorder, or condition in a subject caused by an antigen derived from the subject or an antigen that is not derived from the subject, wherein the anergy induced cell comprises a CD8 positive cell, and the anergy induced cell comprises at least one of a FOXP3 positive cell and a CD4 positive cell.

(F12) The anergy induced cell of any of the preceding items, comprising all of a FOXP3 positive cell, a CD4 positive cell, and a CD8 positive cell.

(F13) The anergy induced cell of any of the preceding items, wherein the CD8 positive cell is CD44 positive.

(F14) The anergy induced cell of any of the preceding items, wherein the CD8 positive cell is CD45RA negative and CD45RO positive.

(F15) The anergy induced cell of any of the preceding items, wherein the FOXP3 positive cell is CD4 positive.

(F16) The use of any of the preceding items, wherein the FOXP3 positive cell is CD25 positive.

(F17) The anergy induced cell of any of the preceding items, which elicits antigen specific immune tolerance or immunosuppression.

(F18) The anergy induced cell of any of the preceding items, wherein the antibody comprises an anti-CD80 antibody, an anti-CD86 antibody, a bispecific antibody to CD80 and CD86, an anti-CD28 antibody, or a combination thereof.

(F19) The anergy induced cell of any of the preceding items, wherein the anergy induced cell is a cell induced by a step of mixing the inhibitory factor, a cell derived from a subject, and an antigen derived from the subject or an antigen that is not derived from the subject or a material containing the antigen.

(F20) An anergy induced cell for treating or preventing a disease, disorder, or condition in a subject caused by an antigen derived from the subject or an antigen that is not derived from the subject, comprising the composition of any of the preceding items.

(F21) The anergy induced cell of any of the preceding items, wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.

(F22) The anergy induced cell of any of the preceding items, wherein the graft rejection is caused by transplanting a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.

(F23) The anergy induced cell of any of the preceding items, wherein the material containing the antigen is a cell.

The present disclosure also provides the following.

(G1) A pharmaceutical composition comprising:
a CD4 positive anergic T cell; and
a CD8 positive anergic T cell.

(G2) The composition of the preceding item, wherein the anergic T cell is induced by an antibody that can inhibit an interaction between CD80 and/or CD86 and CD28.

(G3) The pharmaceutical composition of any of the preceding items, further comprising a regulatory T cell.

(G4) The composition of any of the preceding items, wherein the regulatory T cell is FOXP3 positive CD4 positive CD25 positive.

(G5) A pharmaceutical composition comprising a cell having anergy induced by an antibody that can inhibit an interaction between CD80 and/or CD86 and CD28, wherein the composition comprises a CD8 positive cell, and the composition further comprises at least one of a FOXP3 positive cell and a CD4 positive cell.

(G6) The composition of any of the preceding items, comprising all of a FOXP3 positive cell, a CD4 positive cell, and a CD8 positive cell.

(G7) The composition of any of the preceding items, wherein the CD8 positive cell is CD44 positive.

(G8) The composition of any of the preceding items, wherein the FOXP3 positive cell is CD4 positive.

(G9) The composition of any of the preceding items, wherein the FOXP3 positive cell is CD25 positive.

(G10) The composition of any of the preceding items, wherein the pharmaceutical composition is for antigen specific immune tolerance or immunosuppression.

(G11) The composition of any of the preceding items, wherein the antibody comprises an anti-CD80 antibody, an anti-CD86 antibody, a bispecific antibody to CD80 and CD86, an anti-CD28 antibody, or a combination thereof.

(G12) The composition of any of the preceding items, wherein the cell is a cell induced by a step of mixing the antibody, a cell derived from a subject, and an antigen derived from the subject or an antigen that is not derived from the subject or a material containing the antigen.

(G13) A pharmaceutical composition for treating or preventing a disease, disorder, or condition in a subject caused by an antigen derived from the subject or an antigen that is not derived from the subject, comprising the composition of any one of items G1 to G12.

(G14) The composition of any of the preceding items, wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.

(G15) The composition of item m G14, wherein the graft rejection is caused by transplanting a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.

(G16) The composition of any of the preceding items, wherein the material containing the antigen is a cell.

(G17) A method of manufacturing a medicament comprising a cell, the method comprising:
(A) mixing an antibody that can inhibit an interaction between CD80 and/or CD86 and CD28, a cell derived from a subject, and an antigen derived from the subject or an antigen that is not derived from the subject or a material containing the antigen;
(B) confirming that a cellular product obtained by the mixing comprises a CD8 positive cell; and
(C) confirming that the cellular product comprises at least one of a FOXP3 positive cell and a CD4 positive cell.

(G18) The method of any of the preceding items, wherein the presence of a CD8 positive cell and the presence of at least one of a FOXP3 positive cell and a CD4 positive cell in the cellular product indicate that the cellular product can be used as a medicament.

(G19) The method of any of the preceding items, wherein the medicament is for treating or preventing a disease, disorder, or condition in the subject caused by an antigen derived from the subject or an antigen that is not derived from the subject.

(G20) The method of any of the preceding items, wherein step (B) comprises detecting CD8 with an anti-CD8 antibody, and step (C) comprises detecting at least one of FOXP3 and CD4 with at least one of an anti-FOXP3 antibody and an anti-CD4 antibody.

(G21) The method of any of the preceding items, wherein the detection is performed by FACS.

(G22) A method of controlling quality of a medicament comprising a cell for treating or preventing a disease, disorder, or condition in a subject caused by an antigen expressed in a cell derived from the subject or an antigen that is not derived from the subject, the method comprising:
(A) confirming that the cell comprises a CD8 positive cell; and
(B) confirming that the cell comprises at least one of a FOXP3 positive cell and a CD4 positive cell.

(G23) The method of item G22, wherein step (A) comprises detecting CD8 with an anti-CD8 antibody, and step (B) comprises detecting at least one of FOXP3 and CD4 with at least one of an anti-FOXP3 antibody and an anti-CD4 antibody.

(G24) The method of any of the preceding items, wherein the detection is performed by FACS, Western blot, or PCR.

(G25) A kit for manufacturing a medicament comprising a mixture of cells, the kit comprising:
(A) an antibody that can inhibit an interaction between CD80 and/or CD86 and CD28;
(B) means for detecting CD8; and
(C) means for detecting at least one of FOXP3 and CD4.

(G25A) A kit for controlling quality of a medicament comprising a mixture of cells, the kit comprising:
(A) means for detecting CD8; and
(B) means for detecting at least one of FOXP3 and CD4.

(G26) The kit of any of the preceding items, wherein the presence of a CD8 positive cell and the presence of at least one of a FOXP3 positive cell and a CD4 positive cell in the mixture of cells indicate that the mixture of cells can be used as a medicament.

(G27) The kit of any of the preceding items, wherein the medicament is for treating or preventing a disease, disorder, or condition in the subject caused by an antigen derived from the subject or an antigen that is not derived from the subject.

(Item G27A) The kit of any of the preceding items, wherein the medicament is for treatment or prevention utilizing immune tolerance.

(G28) A kit for controlling quality of a medicament comprising a cell for treating or preventing a disease, disorder, or condition in a subject caused by an antigen expressed in a cell derived from the subject or an antigen that is not derived from the subject, the kit comprising:
(A) means for detecting CD8; and
(B) means for detecting at least one of FOXP3 and CD4.

(G29) The kit of any of the preceding items, wherein the means for detecting CD8 comprises an anti-CD8 antibody, and the means for detecting at least one of FOXP3 and CD4 comprises at least one of an anti-FOXP3 antibody and an anti-CD4 antibody.

(G30) The kit of any of the preceding items, wherein the detection is performed by FACS, Western blot, or PCR.

The present disclosure is intended so that one or more of the features described above can be provided not only as the explicitly disclosed combinations, but also as other combinations thereof. Additional embodiments and advantages of the present disclosure are recognized by those skilled in the art by reading and understanding the following detailed description as needed.

Advantageous Effects of Invention

The composition of the present disclosure comprises a CD4 positive anergic T cell and a CD8 positive anergic T cell, and has an ability to induce higher immune tolerance than a composition free of CD8 positive anergic T cells. The present disclosure can also control the quality of a medicament by using a CD8 positive cell as an indicator in the manufacture of a medicament for inducing immune tolerance.

BRIEF DESCRIPTION OF DRAWINGS

FIG. 3a shows the cumulative survival of heart transplanted mice without transplantation of anergic cells or with administration of $2×10^6$, $4×10^6$, or $6×10^6$ cells of all anergic cells. FIG. 3b shows the effect of irradiating radiation on recipient mice. The survival of mice was tracked after treatment with no irradiation of radiation on recipient mice+$5×10^6$ all anergic cells, irradiation of 2.5 Gy of radiation on recipient mice+$4×10^6$ naïve B6 splenocytes, or irradiation of 2.5 Gy of radiation on recipient mice+$4×10^6$ all anergic cells. FIGS. 3c and 3d show the survival of heart transplanted mice when various purified cell populations were administered.

Figure 6:
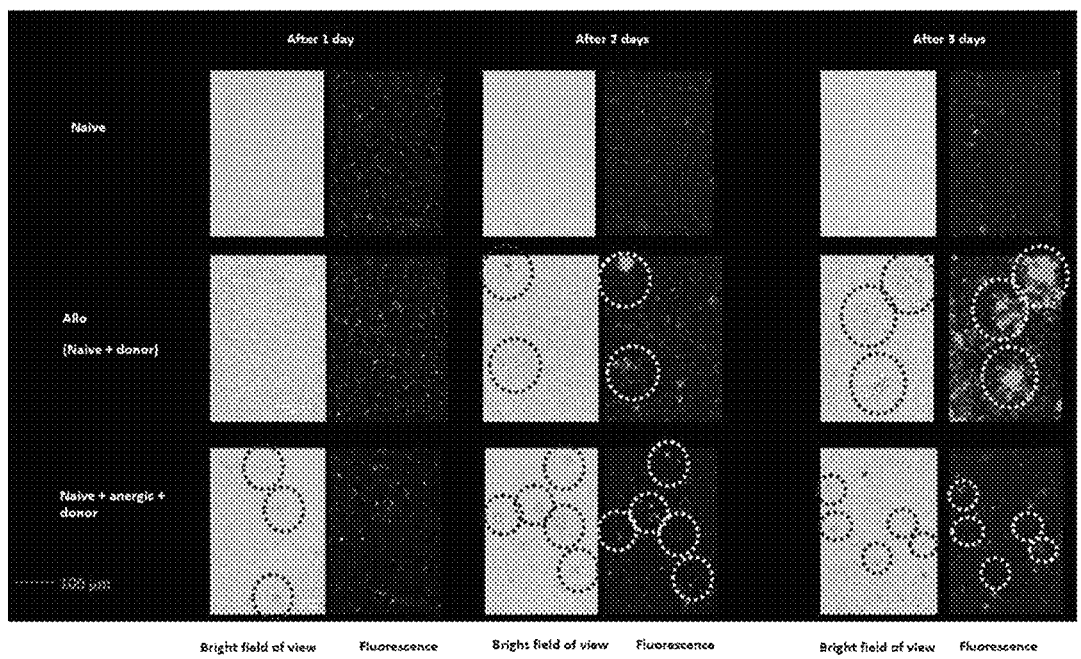

FIG. 6 shows that anergic cells bind to donor (stimulator) cells more quickly than naïve cells to inhibit the reaction and proliferation of naïve cells. Anergic cells were obtained by treating splenocytes obtained from B6 mice with BALB/c derived radiation irradiated splenocytes and anti-CD80 antibodies/anti-CD86 antibodies by the same approach as Example 1. In this experiment, splenocytes newly obtained from B6 mice genetically engineered so that a fluorescent dye GFP would be constantly expressed were used as a responder. The anergic cells were added, so that the ratio to the responder B6 splenocytes would be ½, to 4 ml of mixed culture system comprising the aforementioned responder B6 splenocytes and stimulator (donor) BALB/c splenocytes at $1 \times 10^6$ cells/ml each in a 12-well plate. The cells were cultured in a 37° C. 5% $CO_2$ incubator. The plate was observed and the pictures thereof were taken over time from the start of culture to after 1 day to after 3 days.

Figure 7A:
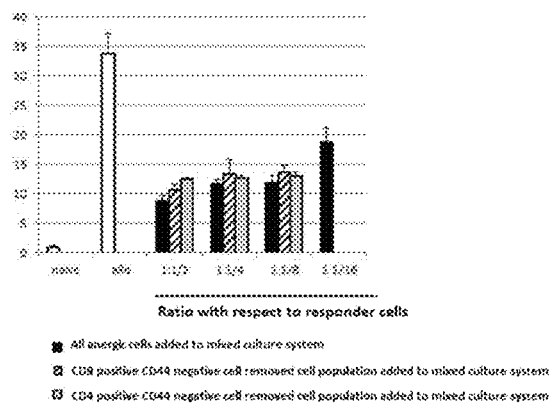
Figure 7B:
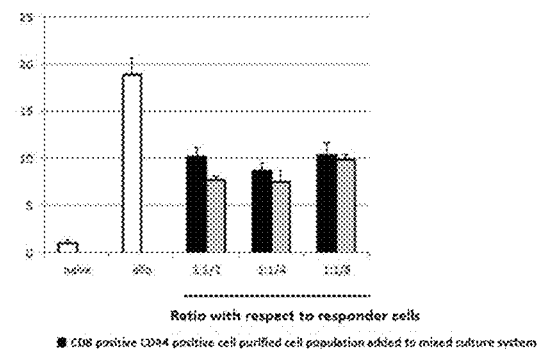
Figure 7C:
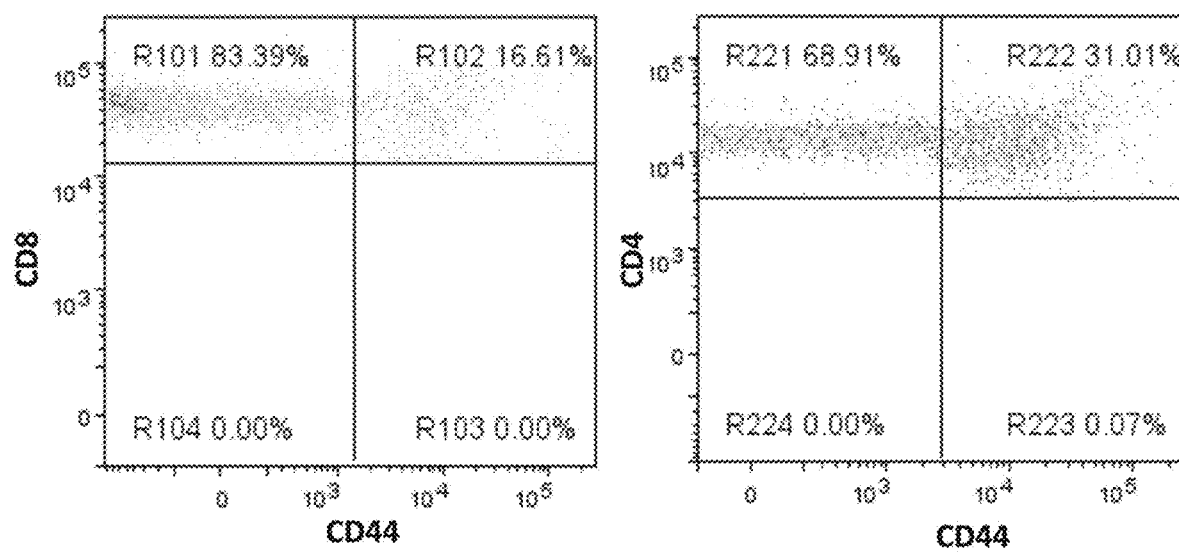

FIG. 7 shows that cells exerting an immunosuppression ability (anergy inducing ability) among anergic cells are CD44 positive. Anergic cells were obtained by treating splenocytes obtained from B6 mice with BALB/c derived radiation, irradiated splenocytes and anti-CD80 antibodies/anti-CD86 antibodies by the same approach as Example 1. The anergic cells were stained with a PE fluorescence labeled anti-mouse CD8 antibody, PE fluorescence labeled anti-mouse CD4 antibody, or APC fluorescence labeled anti-mouse CD44 antibody. A cell population was then prepared by removing CD8 positive CD44 negative cells or CD4 positive CD44 negative cells using a JSAN cell sorter. This cell population or all anergic cells was added to the mixed culture system so that the ratio to the responder B6 splenocytes would be ½, ¼, ⅛, or ¹⁄₁₆ (FIG. 7a). Furthermore, a CD8 positive CD44 positive cell or CD4 positive CD44 positive cell purified cell population was prepared using a JSAN cell sorter, and added to the mixed culture system so that the ratio to the responder B6 splenocytes would be ½, ¼, or ⅛ (FIG. 7b). FIG. 7c shows results of studying the phenotype of anergic cells by FACS.

Figure 8:
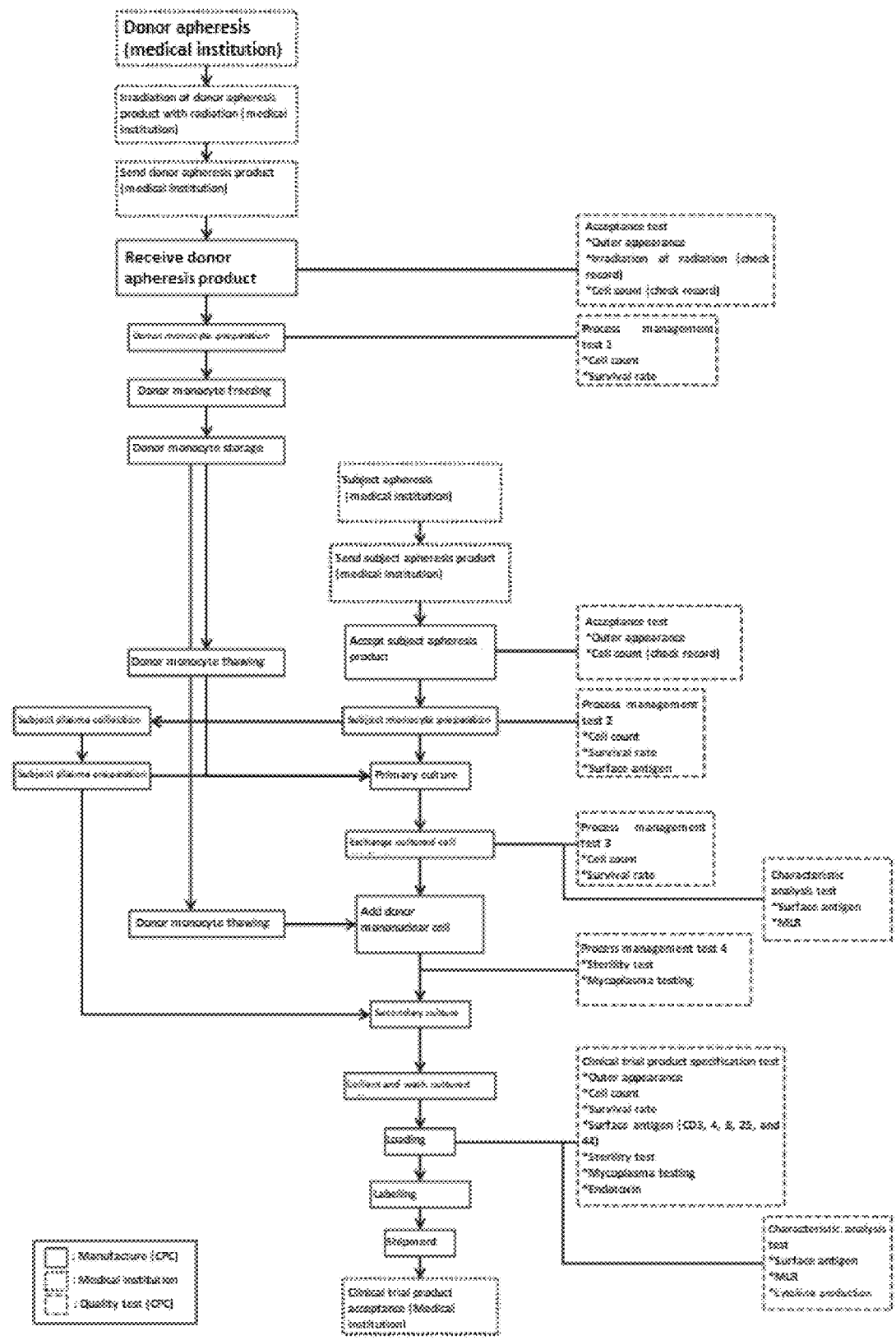

FIG. 8 shows a representative example of the flow of manufacturing and quality testing.

DESCRIPTION OF EMBODIMENTS

The present disclosure is described hereinafter while providing the best mode of the present disclosure. Throughout the entire specification, a singular expression should be understood as encompassing the concept thereof in the plural form, unless specifically noted otherwise. Thus, singular articles (e.g., "a", "an", "the" and the like in case of English) should also be understood as encompassing the concept thereof in the plural form, unless specifically noted otherwise. The terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence.

Definitions of Terms

As used herein, "about" refers to a range of +10% of the subsequent numerical value.

As used herein, "immune tolerance" refers to a state where a specific immune response to a specific antigen is not exhibited or a specific immune response is suppressed. Immune tolerance can also refer to either or both of a state where an immune cell (especially T cell) does not exhibit a specific immune response to a specific antigen or a specific immune response is suppressed, and a state where a human does not exhibit a specific immune response to a specific antigen or a specific immune response is suppressed. Immune tolerance has drawn attention because elicitation of immune tolerance makes it possible to treat immune rejection or treat allergies. As used herein, "anergy" refers to a state where costimulation is not inputted when an antigen is presented from an antigen presenting cell so that a cell cannot respond upon stimulated under the condition with costimulation the next time. Therefore, as used herein, "anergic cell" refers to a (non-immune responsive) cell with immune tolerance, and "anergic T cell" is a (non-immune responsive) T cell with immune tolerance, which also encompasses T cells that are not activated as well as T cells that are non-responsive when encountering the same antigen again. As used herein, "PBMC (or T cell) with immune tolerance induced" is synonymous with "anergic PBMC (or T cell)". It is possible to verify whether a cell is an anergic cell by, for example, verifying that the cell is CD44 positive, but the method is not limited thereto.

As used herein, "subject" includes domesticated animals (e.g., cows, sheep, cats, dogs, and horses), primates (e.g., humans and non-human primates such as monkeys), rabbits, and rodents (e.g., mice and rats). In a specific embodiment, the subject is a human.

As used herein, "agent" is used broadly and may be any substance or other elements (e.g., light, radiation, heat, electricity, and other forms of energy) as long as the intended objective can be achieved. Examples of such a substance include, but are not limited to, protein, polypeptide, oligopeptide, peptide, polynucleotide, oligonucleotide, nucleotide, nucleic acid (including, for example, DNAs such as cDNA and genomic DNA and RNAs such as mRNA), polysaccharide, oligosaccharide, lipid, organic small molecule (e.g., hormone, ligand, information transmitting substance, other organic small molecule compounds, molecule synthesized by combinatorial chemistry, small molecule that can be used as medicine (e.g., small molecule ligand and the like), and composite molecule thereof.

As used herein, "inhibitor," "inhibitory agent," or "inhibitory factor" refers to any type of small molecule, protein, nucleic acid, lipid, saccharide, or the like that can inhibit a given action (e.g., interaction, signaling, or the like). Although not wishing to be bound by a specific theory, anergy is induced in a T cell by blocking the interaction between CD80 and/or CD86 and CD28 on a cell surface to inhibit CD28 costimulation signals in the present disclosure. In the present disclosure, an inhibitory factor used for blocking the interaction between CD80 and/or CD86 and CD28 is selected from the group consisting of a small molecule, protein, nucleic acid, lipid, saccharide, and combination thereof. In one aspect, the protein is an antibody or a variant thereof, or a cell surface molecule or a variant thereof. In another aspect, the variant of the antibody is an antigen binding fragment. In another aspect, the variant of the cell surface molecule is a fusion protein. In another aspect, the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein. In another aspect, the CTLA4-Ig fusion protein is abatacept or belatacept. Combined use of an agent that indirectly inhibits the interaction (e.g., inhibitory factor of an upstream or downstream signal of signaling) is also envisioned.

As used herein, "antibody" broadly refers to a molecule or a group thereof that can specifically bind to a specific epitope on an antigen. As used herein, "antibody" can be broadly a full-length antibody (i.e., antibody with an Fc moiety) or an antibody lacking an Fc moiety. An antibody lacking an Fc moiety only needs to be able to bind to an antigen of interest. Examples of such an antibody include, but are not limited to, Fab antibodies, F(ab')$_2$ antibodies, Fab' antibodies, Fv antibodies, and scFv antibodies, and the like. An antibody can be any type of antibody, i.e., an immunoglobulin known in the art. In an exemplary embodiment, an antibody is an isotype IgA, IgD, IgE, IgG, or IgM class antibody. In an exemplary embodiment, the antibody described herein comprises one or more alpha, delta, epsilon, gamma, and/or mu heavy chains. In an exemplary embodiment, the antibody described herein comprises one or more kappa light chains. In an exemplary embodiment, an antibody is an IgG antibody of one of four human subclasses: IgG1, IgG2, IgG3, and IgG4. Examples of antibodies envisioned to be used in the present disclosure include an antibody derived from an animal of the genus camelidae (e.g., VHH antibody), shark derived antibody (e.g., single stranded antibody), peptibody, nanobody (single domain antibody), minibody, multi-specific antibody (e.g., bispecific antibody, diabody, triabody, tetrabody, tandem di-scFv, tandem tri-scFv), and the like, which are known in the art. See for example Kortt et al., Biomol Eng. 2001 Vol 18: pp 95 to 108, (2001), Todorovska et al., J Immunol Methods. Vol 248: pp 47 to 66, (2001), and the like. Antibodies also include modified and unmodified antibodies. For modified antibodies, an antibody can be bound to various molecules such as polyethylene glycol. A modified antibody can be obtained by applying a chemical modification to an antibody using a known method. See Journal of Japanese Biochemical Society (2016), Vol. 88, No. 3, pp. 380 to 385 for artificially created antibodies and various modification/alteration methods of antibodies.

As used herein, "antibody" narrowly refers to immunoglobulin or a group thereof that can specifically bind to a specific epitope on an antigen. A variant form thereof is referred to as a "variant of an antibody". As used herein, "antibody" can be narrowly a full-length antibody (i.e., antibody with an Fc moiety). A "variant of an antibody" herein can be a variant lacking an Fc moiety of an antibody described above. Therefore, as used herein, an antibody can also be narrowly referred to as a full-length antibody, and a variant of an antibody can also be referred to as a variant of a full-length antibody. A variant lacking an Fc moiety only needs to be able to bind to an antigen of interest. Examples of such a variant include, but are not limited to, Fab antibodies, F(ab')$_2$ antibodies, Fab' antibodies, Fv antibodies, and scFv antibodies, and the like. Variants of an antibody also include modified antibodies and unmodified antibodies. For modified antibodies, an antibody can be bound to various molecules such as polyethylene glycol. A modified antibody can be obtained by applying a chemical modification to an antibody using a known method.

In one embodiment of the present disclosure, "polyclonal antibody" can be generated, for example, by administering an immunogen comprising an antigen of interest to a mammal (e.g., rat, mouse, rabbit, cow, monkey, or the like), avian, or the like to induce the production of a monoclonal antibody specific to an antigen. An immunogen can be administered through one or more immunologic agents, and infusion of an adjuvant when desired. An adjuvant can be used to increase immune responses and can include Freund's adjuvant (complete or incomplete), mineral source (aluminum hydroxide or the like), surfactant (lysolecithin or the like), or the like. The immunization protocol is known in the art and can be performed by any method that induces an immune response in accordance with the selected host organism ("Tanpakushitsu Jikken Handobukku [Protein experiment handbook], Yodosha (2003): 86-91").

In one embodiment of the present disclosure, "monoclonal antibody" encompasses individual antibodies constituting a population that are identical antibodies corresponding to substantially a single epitope, except for antibodies having a mutation that can occur naturally in small amounts. Further, individual antibodies constituting a population may be antibodies that are substantially the same except for antibodies having a mutation that can occur naturally in small amounts. Monoclonal antibodies are highly specific, which are different from common polyclonal antibodies that typically include different antibodies corresponding to different epitopes and/or different antibodies corresponding to the same epitope. In addition to their specificity, monoclonal antibodies are useful in that they can be synthesized from a hybridoma which is not culture contaminated with other immunoglobulins. The description "monoclonal" may indicate a characteristic of being obtained from a substantially homogeneous antibody population. However, such a description does not mean that antibodies must be produced by a specific method. For example, monoclonal antibodies may be prepared by a method similar to the hybridoma method described in "Kohler G, Milstein C., Nature. 1975 Aug. 7; 256 (5517): 495-497". Alternatively, monoclonal antibodies may be prepared by a method similar to the recombinant method described in U.S. Pat. No. 4,816,567. Monoclonal antibodies may also be isolated from a phage antibody library using a method similar to the technology that is described in "Clackson et al., Nature. 1991 Aug. 15; 352 (6336): 624-628." or "Marks et al., J Mol Biol. 1991 Dec. 5; 222 (3): 581-597". Monoclonal antibodies may also be prepared by the method described in "Tanpakushitsu Jikken Handobukku [Protein experiment handbook], Yodosha (2003): 92-96".

In one embodiment of the present disclosure, "chimeric antibody" is, for example, a variable region of an antibody linked to a constant region of an antibody between xenogenic organisms and can be constructed by a genetic engineering technology. A mouse-human chimeric antibody can be prepared by, for example, the method described in "Roguska et al., Proc Natl Acad Sci USA. 1994 Feb. 1; 91 (3): 969-973." For example, the basic method of preparing a mouse-human chimeric antibody links a mouse leader sequence and a variable region sequence in a cloned cDNA with a sequence encoding a human antibody constant region already present in an expression vector of a mammalian cell. After linking the mouse leader sequence and variable region sequence in a cloned cDNA with the sequence encoding a human antibody constant region, the resultant sequence may be linked to a mammalian cell expression vector. A fragment of a human antibody constant region can be from any human antibody H chain constant region and human antibody L chain constant region. Examples of human H chain fragment include Cγ1, Cγ2, Cγ3, and Cγ4, and examples of L chain fragment include CA and CK.

In one embodiment of the invention, "humanized antibody" is, for example, an antibody, which has one or more CDRs derived from a nonhuman species, a framework region (FR) derived from a human immunoglobulin, and a constant region derived from human immunoglobulin and binds to a desired antigen. Antibodies can be humanized using various approaches known in the art (Almagro et al., Front Biosci. 2008 Jan. 1; 13:1619-1633). Examples thereof include CDR grafting (Ozaki et al., Blood. 1999 Jun. 1; 93 (11): 3922-3930), Re-surfacing (Roguska et al., Proc Natl Acad Sci USA. 1994 Feb. 1; 91 (3): 969-973), FR shuffle (Damschroder et al., Mol Immunol. 2007 April; 44 (11): 3049-3060. Epub 2007 Jan. 22) and the like. An amino acid residue of a human FR region may be substituted with a corresponding residue from a CDR donor antibody in order to alter (preferably in order to improve) the antigen bond. The FR substitution can be performed by a method that is well known in the art (Riechmann et al., Nature. 1988 Mar. 24; 332 (6162): 323-327.) For example, an FR residue that is important for antigen binding may be identified by modeling an interaction between a CDR and an FR residue. Further, an abnormal FR residue at a specific position may be identified by sequence comparison.

In one embodiment of the invention, "human antibody" is, for example, an antibody in which a region comprising a variable region and constant region of a heavy chain and variable region and constant region of a light chain constituting the antibody is derived from a gene encoding a human immunoglobulin. Examples of main preparation methods include a method using a transgenic mouse for preparing human antibodies, phage display method, and the like. A method using a transgenic mouse for preparing human antibodies produces human antibodies with diverse antigen binding capabilities instead of mouse antibodies if a functional human Ig gene is introduced into an endogenous Ig knockout mouse. Furthermore, this mouse can be immunized to obtain human monoclonal antibodies by a conventional hybridoma method. This can be prepared, for example, by the method described in "Lonberg et al., Int Rev Immunol. 1995; 13 (1): 65-93." The phage display method is a system that typically expresses an exogenous gene as a fusion protein such that phage infectivity is not lost on the N-terminus side of a coat protein (g3p, g10p, or the like) of fibrous phage such as an E. coli virus M13 or T7. Antibodies can be prepared, for example, by the method described in "Vaughan et al., Nat Biotechnol. 1996 March; 14 (3): 309-314".

As used herein, "cell derived from a subject" refers to a cell obtained from a subject administered with the composition of the present disclosure or a cell derived from a cell obtained from the subject. As used herein, "antigen derived from a subject" refers to an antigen produced by a subject themselves which induces an immune response, such as an antigen produced by a subject themselves which causes an autoimmune disease in a subject with the autoimmune disease. As used herein, "antigen that is not derived from a subject" refers to an exogenous antigen that can induce an immune response. As used herein, "antigen-containing material that is not derived from a subject" refers to any substance or collection of substances comprising an antigen that is not derived from a subject. Examples thereof include a cell, cell population, tissue, and the like expressing an antigen that is not derived from a subject.

As used herein, "graft rejection" refers to the immune system of a subject attacking, damaging, or destroying a transplanted organ, tissue, or cell in a subject receiving transplantation of the organ, tissue, or cell.

As used herein, "allergy" refers to a hyperactive immune response to an antigen that is not derived from a subject. An antigen that is not derived from a subject, which induces an allergy, is also referred to as an allergen. Examples thereof include, but are not limited to, tick antigen, egg white antigen, milk antigen, wheat antigen, peanut antigen, soybean antigen, buckwheat antigen, sesame antigen, rice antigen, crustacean antigen, kiwi antigen, apple antigen, banana antigen, peach antigen, tomato antigen, tuna antigen, salmon antigen, mackerel antigen, beef antigen, chicken meat antigen, pork antigen, feline dander antigen, insect antigen, pollen antigen, dog dander antigen, fungal antigen, bacterial antigen, latex, hapten, metal, and the like.

As used herein, "autoimmune disease" refers to any disease in which the immune system exerts an undesirable immune response on its own cell, tissue, or organ. Examples of an autoimmune disease include, but are not limited to, rheumatoid arthritis, multiple sclerosis, type 1 diabetes, inflammatory bowel disease (e.g. Crohn's disease or ulcerative colitis), systemic lupus erythematosus, psoriasis, scleroderma, autoimmune thyroid disease, alopecia areata, Graves' disease, Guillain Barre syndrome, celiac disease, Sjogren's syndrome, rheumatic fever, gastritis, autoimmune atrophic gastritis, autoimmune hepatitis, pancreatitis, ovitis, orchitis, uveitis, lens-induced uveitis, myasthenia gravis, primary myxedema, pernicious anemia, autoimmune hemolytic anemia, Addison's disease, scleroderma, Goodpasture syndrome, nephritis (e.g., glomerulonephritis), psoriasis, pemphigus vulgaris, pemphigoid, sympathetic ophthalmia, idiopathic thrombocytopenia purpura, idiopathic leukopenia, Wegener's granulomas, and polymyositis/dermatomyositis.

As used herein, "graft-versus-host disease" refers to a transplanted organ, tissue, or cell attacking, damaging, or destroying a cell, tissue, or organ of a subject who received transplantation due to an immune response.

As used herein, "immune rejection caused by transplantation of an iPS cell or ES cell, or a cell, tissue, or organ derived from said cells" refers to an immune rejection resulting from an antigen of an iPS cell or ES cell, or an antigen of a cell, tissue, or organ derived from an iPS cell or ES cell.

Preferred Embodiments

The preferred embodiments are described hereinafter. It is understood that the embodiments are exemplification of the present disclosure, so that the scope of the present disclosure is not limited to such preferred embodiments. It is understood that those skilled in the art can refer to the embodiments readily following preferred to make modifications or changes within the scope of the present disclosure. Any of these embodiments can be appropriately combined by those skilled in the art by referring to the descriptions herein. It is understood that the following embodiments in the present disclosure can be used alone or as a combination thereof.

(Medicament and Treatment and Prevention)

The inventors found that the ability to induce immune tolerance is diminished without a CD8 positive cell in a mixture comprising anergy induced T cells, even if anergy is induced in a T cell using an inhibitory factor that inhibits the interaction between CD80/CD86 and CD28. This was in contrast to and unexpected from Non Patent Literature 4, which reports the possibility of almost no effect on immunosuppression from removing a CD8 positive cell.

In one embodiment, the present disclosure provides a pharmaceutical composition comprising a CD4 positive anergic T cell and a CD8 positive anergic T cell. Such a pharmaceutical composition can be used for antigen specific immune tolerance or immunosuppression. The anergic T cell can be induced by an inhibitory factor that can inhibit the interaction between CD80 and/or CD86 and CD28. Such an inhibitory factor is selected from the group consisting of a small molecule, a protein, a nucleic acid, a lipid, a saccharide, and a combination thereof. In one aspect, the protein is an antibody or a variant thereof, or a cell surface molecule or a variant thereof. In another aspect, the variant of the antibody is an antigen binding fragment. In another aspect, the variant of the cell surface molecule is a fusion protein. In another aspect, the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein. In another aspect, the CTLA4-Ig fusion protein is abatacept or belatacept.

In some embodiments, CD80 and/or CD86 are expressed by an antigen presenting cell, and CD28 is expressed by a T cell.

In some embodiments, the pharmaceutical composition of the present disclosure can further comprise a regulatory T cell, such as a FOXP3 positive CD4 positive CD25 positive T cell. Such a regulatory T cell is not directly involved with "immune tolerance" in which a specific immune response to a specific antigen is not exhibited and is not an essential component, but can suppress immune responses. Thus, in a preferred embodiment, the composition of the present disclosure can further comprise a regulatory T cell.

In another aspect of the present disclosure, the present disclosure provides a pharmaceutical composition comprising a cell having anergy induced by an inhibitory factor that can inhibit an interaction between CD80 and/or CD86 and CD28, wherein the composition comprises a CD8 positive cell, and the composition further comprises at least one of a FOXP3 positive cell and a CD4 positive cell. Such a pharmaceutical composition can be used for antigen specific immune tolerance or immunosuppression. In a specific embodiment, the composition of the present disclosure can comprise all of a FOXP3 positive cell, a CD4 positive cell, and a CD8 positive cell.

The inventors found that anergy induced CD8 positive cells and CD4 positive cells (also referred to as CD8 positive anergic cells and CD4 positive anergic cells) include many CD44 positive cells. Thus, in some embodiments, the CD8 positive cell and/or CD4 positive cell can be CD44 positive. Production of an anergic cell can be confirmed using CD44 as well as CD45RA/CD45RO. For example, in one aspect, the CD8 positive cell and/or CD4 positive cell is CD45RA negative and CD45RO positive.

In some embodiments, a FOXP3 positive cell can be CD4 positive and/or CD25 positive. It is preferably that the composition of the present disclosure further comprises a regulatory T cell. A regulatory T cell can be FOXP3 positive and can further be CD4 positive and/or CD25 positive.

In some embodiments, an inhibitory factor that can inhibit an interaction between CD80 and/or CD86 and CD28 is selected from the group consisting of a small molecule, a protein, a nucleic acid, a lipid, a saccharide, and a combination thereof. In one aspect, the protein is an antibody or a variant thereof, or a cell surface molecule or a variant thereof. In another aspect, the variant of the antibody is an antigen binding fragment. In another aspect, the variant of the cell surface molecule is a fusion protein. In another aspect, the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein. In another aspect, the CTLA4-Ig fusion protein is abatacept or belatacept. In some embodiments, CD80 and/or CD86 are expressed by an antigen presenting cell, and CD28 is expressed by a T cell. In a specific embodiment, an inhibitory factor that can inhibit an interaction between CD80 and/or CD86 and CD28 can be an anti-CD80 antibody and/or an anti-CD86 antibody, or a CTLA4-Ig fusion protein. Examples of inhibitory factors envisioned for use in the present disclosure include a CTLA4-Ig fusion protein as described above. A CTLA4-Ig fusion protein competes with CD28, i.e., a costimulatory receptor on a T cell, for binding to CD80/CD86 on an antigen presenting cell, resulting in functioning to inhibit the activation of T cells. In the present disclosure, abatacept (Orencia®), belatacept, or Maxy-4 is envisioned as the CTLA4-Ig fusion protein. Belatacept comprises two amino acid substitutions (L104E and A29Y) that significantly increase the avidity to bind to CD80 and CD86 (see Davies J K et al., Cell Transplant. (2012); 21 (9): 2047 to 61, Adams A B et al., J Immunol. (2016) 197 (6): 2045 to 50). Examples of inhibitory factors expected to have the same effect as a CTLA4-Ig fusion protein include CD28-Ig fusion protein (see Peach R J et al., J Exp Med. (1994) 180 (6): 2049 to 2058). The inhibitory factor of the present disclosure can also be used in a form of a nucleic acid. In one example, a nucleic acid encoding a CTLA4-Ig fusion protein is envisioned to be introduced into and expressed in a cell via an adenoviral vector or the like. See, for example, Jin Y Z et al., Transplant Proc. (2003); 35 (8): 3156 to 9.

In some embodiments, an anergic cell can be a cell induced by a step of mixing an inhibitory factor such as an antibody, a cell derived from a subject, and an antigen derived from the subject or an antigen that is not derived from the subject or a material containing the antigen. The material containing the antigen can be a cell, and can be irradiated with radiation in order to prevent proliferation and activation of the cell.

In a specific embodiment, a pharmaceutical composition for treating or preventing a disease, disorder, or condition in a subject caused by an antigen derived from the subject or an antigen that is not derived from the subject, comprising the composition of the present disclosure can be provided. Examples of the disease, disorder, or condition in a subject caused by an antigen derived from the subject or an antigen that is not derived from the subject include, but are not limited to, diseases, disorders, or conditions requiring immune tolerance such as graft rejection, allergy, autoimmune disease, graft-versus-host disease, and immune rejection caused by transplantation of an iPS cell or an ES cell and a cell, tissue, or organ derived from said cells.

In some embodiments, graft rejection is caused by transplanting a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.

In an embodiment where the disease or the like targeted by the present disclosure is graft rejection, an anergic cell can be induced by mixing an inhibitory factor such as an antibody, a cell derived from a recipient (PBMC or splenocyte), and an antigen derived a donor or a material containing the antigen derived from a donor. The material containing an antigen derived from a donor can be a PBMC, a splenocyte, a cell derived from an organ to be transplanted, or the like.

In embodiment where the disease or the like targeted by the present disclosure is allergy, an anergic cell can be induced by mixing an inhibitory factor such as an antibody, a cell derived from a subject (PBMC or splenocyte), and an allergy-causing antigen that is not derived from a subject.

In embodiment where the disease or the like targeted by the present disclosure is an autoimmune disease, an anergic cell can be induced by mixing an inhibitory factor such as an antibody, a cell derived from a subject (PBMC or splenocyte), and an antigen derived from a subject that can be a cause of an autoimmune disease.

In an embodiment where the disease or the like targeted by the present disclosure is a graft-versus-host disease, an anergic cell can be induced by mixing an inhibitory factor such as an antibody, a PBMC or splenocyte of a donor providing the graft and recipient derived antigen or a material containing the antigen. The material containing an antigen derived from a recipient can be a PBMC, splenocyte, a cell around a site where an organ is transplanted, a cell derived therefrom, or the like.

In an embodiment where the disease or the like targeted by the present disclosure is immune rejection caused by transplantation of an iPS cell or an ES cell and a cell, tissue, or organ derived from said cells, an anergic cell can be induced by mixing an inhibitory factor such as an antibody, a subject derived cell (PBMC or splenocyte), and a cell differentiated from an iPS cell or ES cell used in transplantation.

Therapeutic examples of a disease or the like according to the present disclosure are shown below, but are not limited thereto.

(Allergy and Autoimmune Disease)

For allergy and autoimmune diseases, a macrophage obtained from the peripheral blood of a patient is differentiated into a dendritic cell (macrophage derived dendritic cell) with high antigen presenting ability by a conventional method. The cell after irradiation of radiation (γ rays) is made to present an antigen that is the cause of hyper-reaction in allergy or autoimmune disease, and co-cultured for 1 to 2 weeks with a T cell group contained form the same patient peripheral blood in the presence of a suitable inhibitory factor such as a CTLA4-Ig fusion protein or an anti-CD80 antibody and/or anti-CD86 antibody to obtain an anergic cell that is specific to the antigen causing the allergy or autoimmune disease. The anergic cell is administered to a patient to induce immune tolerance specific to the antigen causing the allergy or autoimmune disease for use in the prevention or treatment of allergy and autoimmune disease. The number of dosings can be multiple, depending on whether the dosing is preventive therapy or treatment, and various conditions such as the severity of symptoms.

(Graft-Versus-Host Disease)

For graft-versus-host disease, in contrast to the treatment of graft rejection, a cell that can be the cause of graft-versus-host disease such as a PBMC or T cell of a donor providing a graft is co-cultured for 1 to 2 weeks with a PBMC derived from a host irradiated with radiation (γ rays) or other cells in the presence of a suitable inhibitory factor such as a CTLA4-Ig fusion protein or an anti-CD80 antibody and/or anti-CD86 antibody to obtain an anergic cell that is specific to a host. Administration of such an anergic cell to a host suppresses responses to a host by a graft causing the graft-versus-host disease (and induces immune tolerance) to prevent or treat graft-versus-host disease. The number of dosings can be multiple, depending on whether the dosing is preventive therapy or treatment, and various conditions such as the tissue to be transplanted, the size thereof, or the severity of symptoms.

(Immune Rejection Caused by Transplantation of an iPS Cell or an ES Cell and a Cell, Tissue, or Organ Derived from Said Cells)

In applications to treatment using an iPS cell or ES cell, a dendritic cell or a cell used in transplantation differentiated from an iPS cell or ES cell is irradiated with radiation (γ rays), and the cell is co-cultured for 1 to 2 weeks with a PBMC or T cell group of a patient receiving transplantation in the presence of a suitable inhibitory factor such as a CTLA4-Ig fusion protein or an anti-CD80 antibody and/or anti-CD86 antibody to obtain an anergic cell that is specific to a cell differentiated from an iPS cell or ES cell. Administration of such an anergic cell to a host induces immune tolerance that is specific to an iPS cell or ES cell derived transplanted cell, tissue, and organ and prevent and treat rejection thereto. The number of dosings can be multiple, depending on whether the dosing is preventive therapy or treatment, and various conditions such as the tissue to be transplanted, the size thereof, or the severity of symptoms.

(Method of Manufacturing a Medicament)

In another aspect of the present disclosure, the present disclosure provides a method of manufacturing a medicament comprising a cell, the method comprising: (A) mixing an inhibitory factor such as an antibody that can inhibit an interaction between CD80 and/or CD86 and CD28, a cell derived from a subject, and an antigen derived from the subject or an antigen that is not derived from the subject or a material containing the antigen; (B) confirming that a cellular product obtained by the mixing comprises a CD8 positive cell; and (C) confirming that the cellular product comprises at least one of a FOXP3 positive cell and a CD4 positive cell. The inventors found that it is important for a mixture of anergy induced T cells to contain a CD8 positive cell in order to exert a sufficient immunosuppression ability. Therefore, it is important to guarantee that a CD8 positive cell is contained in the manufacture of a medicament comprising an anergy induced T cell. A medicament manufactured in such a manner can be used to treat or prevent a disease, disorder, or condition in a subject caused by an antigen derived from a subject or an antigen that is not derived from the subject. Any inhibitory factor that would produce a CD8 positive cell can be used.

In some embodiments, the presence of a CD8 positive cell and the presence of at least one of a FOXP3 positive cell and a CD4 positive cell in the cellular product indicate that the cellular product can be used as a medicament.

In step (B), CD8 can be detected by using an anti-CD8 antibody to confirm that a CD8 positive cell is included. In step (C), at least one of FOXP3 and CD4 can be detected by using at least one of an anti-FOXP3 antibody and an anti-CD4 antibody in order to confirm that at least one of FOXP3 positive cell and a CD4 positive cell is included. Examples of specific methodologies of detection include, but are not limited to, flow cytometry (FACS), Western blot, RNA detection, and the like. Preferably, the specific methodology of detection is FACS. RNA is detected by a method that is known in the art, such as PCR. FOXP3 is expressed in a cell, so that a cell can be immobilized and then permeabilized to stain the inside of the cell. FOXP3 can also be detected by an approach such as FACS. Examples of suitable commercial products for use in this method include eBioscience™ Human Regulatory T Cell Staining Kit #3

(cat #88-8995-40), eBioscience™ Mouse Regulatory T Cell Staining Kit #1 (cat #88-8111-40), eBioscience™ Human/Non-Human Primate Regulatory T Cell Staining Kit #1 (cat #88-4999-40), eBioscience™ Human Regulatory T Cell Whole Blood Staining Kit (cat #88-8996-40), and the like.

(Quality Control Method)

In another aspect, the present disclosure provides a method of controlling quality of a cell formulation (cell containing medicament). More specifically, the present disclosure provides a method for controlling quality of a medicament comprising a cell for treating or preventing a disease, disorder, or condition in a subject caused by an antigen expressed in a cell derived from the subject or an antigen that is not derived from the subject, the method comprising: (A) confirming that the cell comprises a CD8 positive cell; and (B) confirming that the cell comprises at least one of a FOXP3 positive cell and a CD4 positive cell. Controlling whether such a medicament comprising a cell comprises a CD8 positive cell is one of the important points to maintain a certain quality (sufficient immune tolerance) in a medicament comprising a cell for treating or preventing a disease, disorder, or condition in a subject caused by an antigen expressed in a cell derived from the subject or an antigen that is not derived from the subject.

In step (A), CD8 can be detected by using an anti-CD8 antibody in order to confirm that a CD8 positive cell is included. In step (B), at least one of FOXP3 and CD4 can be detected by using at least one of an anti-FOXP3 antibody and an anti-CD4 antibody in order to confirm that at least one of a FOXP3 positive cell and a CD4 positive cell is included. Examples of specific means for detection include, but are not limited to, FACS, Western blot, PCR, and the like. FOXP3 is expressed in a cell, so that a cell can be immobilized and then permeabilized to stain the inside of the cell. FOXP3 can also be detected by an approach such as FACS.

A typical example of a method of manufacturing and controlling the quality of a cell formulation of the present disclosure is shown hereinafter.

(Manufacture and Quality Control of a Cell Formulation Comprising an Anergic T Cell)

1. Organism Derived Raw Material and Compliance Status Thereof

In one embodiment, an organism derived raw material that is in compliance with the standards for organism derived raw materials described in Table 1 is used in the step of manufacturing an anergic T cell.

An anergic T cell is administered after organ transplantation (e.g., liver transplantation) from a donor to a recipient. A donor organ (e.g., liver) includes donor derived mononuclear cell, which is the material for a self-derived anergic T cell, without removing viruses. A donor organ (e.g., liver) is transplanted into a recipient while including donor derived mononuclear cells. For this reason, a donor derived mononuclear cell used as a material for a self-derived anergic T cell is not considered to fall under an organism derived raw material.

TABLE 1

Table 1 List of organism derived raw materials

| Name | Contained organism derived raw material | | Status of compliance to standards for organism derived raw materials |
|---|---|---|---|
| | Component name | Animal species | |
| Anti-CD80 antibody | Cell derived component | Chinese hamster (heterologous) | Scheduled to select an antibody manufactured by a step of verifying quality and safety in accordance with ICH-Q5A and ICH-Q5D |
| Anti-CD86 antibody | Cell derived component | Chinese hamster (heterologous) | Scheduled to select an antibody manufactured by a step of verifying quality and safety in accordance with ICH-Q5A and ICH-Q5D |
| ALyS505N-0 | Human serum albumin | Human (autologous) | Selected a pharmaceutical product (plasma fractionated formulation) |
| AIM-V | Human serum albumin | Human (autologous) | Selected a material compatible with the standards for organism derived raw materials *Details described in the master file |
| Human serum albumin | Human serum albumin | Human (autologous) | Selected a pharmaceutical product (plasma fractionated formulation) |

Belatacept (available from, e.g., Bristol-Myers Squibb, New York, NY)

2. Method of Manufacturing a Cell Formulation

In one embodiment, a cell formulation can be manufactured in the following manner. Various numerical values and the like that are exemplified hereinafter are representative examples. Those skilled in the art can manufacture cell formulations by appropriately changing the values or the like.

1) At about 19 days before administration, apheresis is performed on a donor at a medical institution. After the donor apheresis product is irradiated with 30 Gy of radiation to eliminate the ability of cells to proliferate, the product is sent to a cell culture processing facility where the cells are processed.

2) After receiving the donor apheresis product, donor mononuclear cells are separated and collected by density gradient centrifugation, separated into two groups, and stored at −80±10° C. at the cell culture processing facility.

3) At about 14 days before administration, apheresis is performed on a recipient at a medical institution. The recipient apheresis product is sent to a cell culture processing facility where the cells are processed.

4) After receiving the recipient apheresis product, recipient mononuclear cells are separated and collected by density gradient centrifugation, and co-cultured with the thawed donor mononuclear cells and an inhibitory factor such as an anti-CD80 antibody and an anti-CD86 antibody or CDLA4-Ig fusion protein at the cell culture processing facility.

5) The medium is exchanged at about 7 days before administration. The intermediate product cultured for 7 days is collected and co-cultured with the thawed donor mononuclear cells and an inhibitory factor such as an anti-CD80 antibody and an anti-CD86 antibody or CDLA4-Ig fusion protein.

6) The processed cell product is collected by density gradient centrifugation on the day of administration, and then washed and loaded into saline.
7) The product is sent to the medical institution, and administered to the recipient at medical institution.

3. Process Management Test

In one embodiment, the process management tests described in Table 2 can be performed within the manufacturing steps. Various numerical values and the like and the procedure that are exemplified hereinafter are representative examples. Those skilled in the art can perform a process management test by appropriately changing the values or the like.

TABLE 2

Table 2 List of process management tests

| Type of test | Tested item | Timing |
|---|---|---|
| Process management test | Cell count | Process management test 1, 2, 3 |
| | Viable cell rate | Process management test 1, 2, 3 |
| | Sterility test | Process management test 1, 2, 4 |
| | Mycoplasma test | Process management test 4 |

4. Specification Test and Characteristic Analysis Test

In one embodiment, the specification test described in Table 3 can be performed using a final product. The procedure exemplified in Table 3 is a representative example. Those skilled in the art can perform the specification test and characteristic analysis test by appropriately changing the procedure. Examples of modified examples thereof include the specification exemplified in Example 8. If the result is not found upon administration of induced suppressor T cells, judgment can be made upon shipping of a clinical trial product by referring to results of a process management test.

The characteristic analysis test described in Table 3 can also be conducted using a cell or final product in the manufacturing process.

TABLE 3

Table 3 List of final product specification tests

| Item | Tested item | Specification value |
|---|---|---|
| Outer appearance | Outer appearance test | Slightly yellowish white to light yellow cell suspension |
| Cell surface marker | Ratio of $CD3^+$ cells | ≥50% |
| | Ratio of $CD8^+$ $CD44^+$ cells in $CD3^+$ cells | ≥10% |
| | Ratio of $CD4^+$ $CD25^+$ cells in $CD3^+$ cells | ≥5% |
| Safety | Sterility test | No growth of microorganism found |
| | Endotoxin | <0.25 EU/mL |
| | Mycoplasma testing | Negative |
| Content | Cell count | ≥1 × $10^9$ cells |
| | Viable cell rate | ≥70% |

The clinical trial product specification test and characteristic analysis test are described herein. A clinical trial product specification test can comprise the outer appearance, cell count, viable cell ratio, cell surface CD8, CD25, CD44, CD45RA/CD45RO), marker (CD3, CD4, manufacturing process derived impurities (donor derived cell, medium component, anti-CD80 antibody, anti-CD86 antibody, cell freeze damage protection solution component, specific gravity separation solution component), virus test, sterility test, mycoplasma test, and endotoxin. An efficacy test can comprise cytokine production or tritium incorporation test through mixed lymphocyte test (MLR) using cultured cells. The baseline value of cell phenotypes can be, for example for the ratio of CD3 positive cells, typically 50% or greater in the table, or for example 30% or greater, 35% or greater, 40% or greater, 45% or greater, 50% or greater, 55% or greater, 60% or greater, 65% or greater, 70% or greater, or a numerical value therebetween (can be set at a 1% or 0.5% increment or the like). The baseline value of the ratio of CD8 positive CD44 positive cells in CD3 positive cells can be typically 10% or greater in the table, or for example 1% or greater, 2% or greater, 3% or greater, 4% or greater, 5% or greater, 6% or greater, 7% or greater, 8% or greater, 9% or greater, 10% or greater, 11% or greater, 12% or greater, 13% or greater, 14% or greater, 15% or greater, or the like. The ratio of CD4 positive CD44 positive cells in CD3 positive cells can be undetermined, or the baseline value can be, for example, 1% or greater, 2% or greater, 3% or greater, 4% or greater, 5% or greater, 6% or greater, 7% or greater, 8% or greater, 9% or greater, 10% or greater, 11% or greater, 12% or greater, 13% or greater, 14% or greater, 15% or greater, or the like. The ratio of CD8 positive CD45RA negative cells in CD3 positive cells can be undetermined, or the baseline value can be, for example, 1% or greater, 2% or greater, 3% or greater, 4% or greater, 5% or greater, 6% or greater, 7% or greater, 8% or greater, 9% or greater, 10% or greater, 11% or greater, 12% or greater, 13% or greater, 14% or greater, 15% or greater, 20% or greater, 25% or greater, 30% or greater, 35% or greater, 40% or greater, or the like. The ratio of CD8 positive CD45RA negative CD45RO positive cells in CD3 positive cells can be undetermined, or the baseline value can be, for example, 1% or greater, 2% or greater, 3% or greater, 4% or greater, 5% or greater, 6% or greater, 7% or greater, 8% or greater, 9% or greater, 10% or greater, 11% or greater, 12% or greater, 13% or greater, 14% or greater, 15% or greater, or the like. The ratio of CD4 positive CD45RA negative CD45RO positive cells in CD3 positive cells can be undetermined, or the baseline value can be, for example, 1% or greater, 2% or greater, 3% or greater, 4% or greater, 5% or greater, 6% or greater, 7% or greater, 8% or greater, 9% or greater, 10% or greater, 11% or greater, 12% or greater, 13% or greater, 14% or greater, 15% or greater, or the like. The baseline value of the ratio of CD4 positive CD25 positive cells in CD3 positive cells can be typically 5% or greater in the table, or for example 1% or greater, 2% or greater, 3% or greater, 4% or greater, 5% or greater, 6% or greater, 7% or greater, 8% or greater, 9% or greater, 10% or greater, 11% or greater, 12% or greater, 13% or greater, 14% or greater, 15% or greater, or the like. For the cell count, $1\times10^9$ cells or greater can be used as a representative baseline, or the cell count can be for example, $1\times10^8$ cells or greater, $5\times10^8$ cells or greater, $1\times10^9$ cells or greater, $2\times10^9$ cells or greater, $3\times10^9$ cells or greater, or the like. For the viable cell ratio, 70% or greater can be used as a representative baseline, or 50% or greater, 55% or greater, 60% or greater, 65% or greater, 70% or greater, 75% or greater, 80% or greater, 85% or greater, 90% or greater, or the like can be used as the baseline.

(Composition of Final Product)

In one example, the final product is comprised of the constituents described in the following table. Those skilled in the art can also appropriately change these specification to change the composition of the prepared regenerative medical product.

TABLE 3-1

Table List of composition

| Constituent | Composition |
|---|---|
| Self-derived anergic cell | 1 × 10$^9$ cells cells or greater |
| Saline | 100 mL |
| Human serum albumin | 1% |

Those skilled in the art can conduct a specification test and characteristic analysis test by applying a change as needed while referring to the technical matters described herein as appropriate.

5. Method of Administering Regenerative Medical Product

In one embodiment, a product is administered once after 14 days from organ transplantation. Those skilled in the art can use a specific administration method, period thereof, and the like by applying a change as needed while referring to the technical matters described herein as appropriate.

(Kit)

In another aspect, the present disclosure provides a kit for manufacturing a cell formulation. In yet another aspect, the present disclosure provides a kit for controlling quality of a cell formulation. Specifically, the present disclosure provides a kit for manufacturing a medicament comprising a mixture of cells, the kit comprising: (A) an inhibitory factor that can inhibit an interaction between CD80 and/or CD86 and CD28; (B) means for detecting CD8; and (C) means for detecting at least one of FOXP3 and CD4.

In some embodiments, the presence of a CD8 positive cell and the presence of at least one of a FOXP3 positive cell and a CD4 positive cell in the mixture of cells indicate that the mixture of cells can be used as a medicament.

A medicament comprising a mixture of cells manufactured by the kit of the present disclosure comprises an anergy induced CD8 positive T cell and at least one of a FOXP3 positive cell and a CD4 positive cell, and can be used for treating or preventing a disease, disorder, or condition in a subject caused by an antigen derived from the subject or an antigen that is not derived from the subject.

In another aspect, the present disclosure provides a kit for controlling quality of a medicament comprising a cell for treating or preventing a disease, disorder, or condition in a subject caused by an antigen expressed in a cell derived from the subject or an antigen that is not derived from the subject, the kit comprising: (A) means for detecting CD8; and (B) means for detecting at least one of FOXP3 and CD4.

In some embodiments, the means for detecting CD8 comprises an anti-CD8 antibody, and the means for detecting at least one of FOXP3 and CD4 comprises at least one of an anti-FOXP3 antibody and an anti-CD4 antibody. The detection can be performed, for example, by FACS, Western blot, PCR, or the like.

(Procedure for Manufacturing Self-Derived Regulatory T Cell)

A typical method of manufacturing a self-derived regulatory T cell is described hereinafter.

Prior Confirmation

In one embodiment, prior confirmation can be performed as described below. Various numerical values, reagents, procedures, and the like exemplified below are representative examples. Those skilled in the art can perform prior confirmation while making appropriate changes.

An infection screening test is administered to a donor and a patient. For the donor, HBs antigen, HCV antibody, HIV-1/2, and HTLV-1 antibody are all confirmed to be negative.

1. Representative Example of Separation of Donor Lymphocyte (Performed Under Aseptic Conditions)

In one embodiment, a donor lymphocyte can be separated in the following matter. Various numerical values, reagents, procedures, and the exemplified like below are representative examples. Those skilled in the art can separate a donor lymphocyte while making appropriate changes.

A donor lymphocyte is collected in a collection bag by apheresis, and radiation is irradiated onto the collection bag.

The radiation irradiated peripheral blood mononuclear cell is placed in a centrifuge tube containing a suitable amount of Ficoll-Paque PREMIUM (GE Healthcare #17-5442-02), Lymphocyte separation Solution (Nacalai Tesque #20828), or the like (e.g., 20 mL), and centrifuged at 860 G for 20 minutes at 22° C. (acceleration of the centrifuge is set to slow, and brake is set to slow).

The supernatant is discarded, and the cell suspension comprising a lymphocyte layer is transferred to another centrifuge tube (e.g., two 50 mL centrifuge tubes).

Saline is added (e.g., suitable amount until the total amount reaches 50 mL) to the centrifuge tube containing the cell suspension. Aspiration and discharge are repeated with a syringe (e.g., 50 mL syringe with an 18 G injection needle) or a pipette for thorough admixing.

The cells are centrifuged at 500 G for 10 minutes at 22° C. (acceleration of the centrifuge can be set to fast, and brake can be set to fast).

The supernatant is discarded. Saline is added again (e.g., suitable amount until the total amount reaches 50 mL). Aspiration and discharge are repeated with a pipette for thorough admixing of a cell pellet.

The cells are centrifuged at 500 G for 5 minutes at 22° C. (acceleration of the centrifuge can be set to fast, and brake can be set to fast).

The supernatant is discarded.

ALYS505N-0 culture (Cell Science & Technology Institute (CSTI) 1020P10) comprising plasma collected from the donor in advance is added to a cell pellet (e.g., suitable amount until the total amount reaches 31 mL). Aspiration and discharge are repeated with a pipette for thorough admixing.

A suitable amount (e.g., 0.3 mL) is withdrawn with a syringe (e.g., 1 ml syringe with an 18 G injection needle) or a pipette to find the cell count and viable cell count.

2. Cryopreservation of Donor Lymphocyte (Performed Under Aseptic Conditions)

In one embodiment, a donor lymphocyte can be cryopreserved in the following manner. Various numerical values, reagents, procedures, and the like exemplified below are representative examples. Those skilled in the art can cryopreserve a donor lymphocyte while making appropriate changes.

A freezing bag (e.g., Froze bag F-050, 25 mL freezing bag, Nipro, 89-101) is opened under aseptic conditions, and required information (date, manufacture number, donor name) is written on a label.

A cell suspension is collected with a syringe (e.g., 30 mL syringe with an 18 G injection needle) and placed into the freezing bag.

An ACD solution (Terumo Corporation, TP-A05ACD, e.g., 2 mL to 15 mL of cell suspension) is added to the freezing bag containing the cell suspension. The bag is cooled for about 10 minutes inbetween ice packs cooled to 4° C.

CP-1 (Kyokuto Pharmaceutical Industrial Co., Ltd. 551-27202-4 cell freeze protection solution CP-1, e.g., 8.5 mL) cooled to 4° C. is added to the freezing bag using a syringe (e.g., 20 mL syringe with an 18 G injection needle) over about a minute and a half. The freezing bag is gently stirred at this time.

All air in the freezing bag and the port thereof is withdrawn using a syringe.

The freezing bag is sealed using a tube sealer. The bag is initially cooled for about 5 to 10 minutes at 4° C., and then stored in a −80° C. freezer.

3. Thawing of Donor Lymphocyte (Performed Under Aseptic Conditions)

In one embodiment, a donor lymphocyte is thawed in the following manner. Various numerical values, reagents, procedures, and the like exemplified below are representative examples. Those skilled in the art can thaw a donor lymphocyte while making appropriate changes.

A freezing bag for a stored donor cell is thawed, for example, in a 37° C. thermostatic vessel. The following steps are preferably performed under aseptic conditions.

Cell suspension is withdrawn from the thawed freezing bag using a syringe (e.g., 50 mL syringe with an 18 G injection needle), and transferred to a centrifuge tube (e.g., 12.5 mL each to two 50 mL centrifuge tubes).

For example, 5% albumin solution (Nihon Pharmaceutical Co., Ltd, 123146364, blood donation albumin 5% intravenous injection 12.5 g/250 mL) (e.g., 37.5 mL to 12.5 mL of cell suspension) is added to the centrifuge tube containing the cell suspension and thoroughly admixed. The suspension is then incubated for about 5 minutes.

For example, the cell suspension is centrifuged at 600 G for 10 minutes at 22° C. (e.g., preferably, acceleration of the centrifuge is set to fast, and brake is set to slow).

The supernatant is gently discarded. A cell pellet is suspended by adding a suitable solution such as albumin added saline for washing (e.g., prepared from 25 mL of 5% albumin solution and 19 mL of saline).

For example, the suspension is centrifuged at 600 G for 10 minutes at 22° C. (e.g., preferably, acceleration of the centrifuge is set to fast, and brake is set to slow)

The supernatant is gently discarded. A cell pellet is suspended by adding an ALYS505N culture (e.g., 10 mL to 50 mL centrifuge tube).

Each of an anti-human CD80 antibody (e.g., m2D10.4; Cat. No. 16-0809-85, eBioscience) and anti-CD86 antibody (e.g., IT2.2; Cat. No. 16-0869-85, eBioscience) is added to a culture bag (e.g., Nipro 87598, Nipro medium ALYS505NB10) containing an ALYS505N-0 culture or a solution equivalent thereto) at, for example, a final concentration of 10 μg/mL (or an equivalent inhibitory factor such as a CTLA4-Ig fusion protein (e.g., belatacept) is added). To the culture bag, the cell suspension is added by injection with a syringe (e.g., 20 mL syringe with an 18 G injection needle). In one example, the total amount of liquid in the culture bag is about 840 mL.

4. Separation of Patient Lymphocyte to Start of Primary Culture (Performed Under Aseptic Conditions)

In one embodiment, a patient lymphocyte can be separated in the following manner. Various numerical values, reagents, procedures, and the like exemplified below are representative examples. Those skilled in the art can separate a patient lymphocyte while making appropriate changes.

Plasma collected from a patient is heated and inactivated, for example, at 56° C. for 30 minutes in a thermostatic vessel. Plasma that is not immediately used is cryopreserved.

Peripheral blood collected from the patient is placed in a centrifuge tube containing a suitable amount of a suitable medium such as Ficoll-Paque (e.g., 20 mL) and centrifuged for example at 860 G for 20 minutes at 22° C. (preferably, acceleration of the centrifuge is set to slow, and brake is set to slow).

The supernatant is discarded, and the cell suspension comprising a lymphocyte layer is transferred to another centrifuge tube (e.g., two 50 mL centrifuge tubes).

Saline is added (e.g., suitable amount until the total amount reaches 50 mL) to the centrifuge tube containing the cell suspension. Aspiration and discharge are repeated with a pipette for thorough admixing.

For example, the cell suspension is centrifuged at 500 G for 10 minutes at 22° C. (acceleration of the centrifuge can be set to fast, and brake can be set to fast).

The supernatant is discarded. Saline is added again (e.g., suitable amount until the total amount reaches 50 mL). Aspiration and discharge are repeated with a pipette for thorough admixing of a cell pellet.

For example, the cell suspension is centrifuged at 500 G for 5 minutes at 22° C. (acceleration of the centrifuge can be set to fast, and brake can be set to fast).

The supernatant is discarded. The cell pellet is suspended by adding for example ALYS505N-0 culture (e.g., 10 mL) to prepare a cell suspension (e.g., ALYS505N-0 culture is added until reaching a total of 20 mL). At this time, about 0.5 mL of cell suspension is withdrawn to find the cell count, viable cell count, and expression of a surface antigen.

A patient derived inactivated plasma is added to the culture bag containing an inhibitory factor such as an antibody and a donor cell in the ALYS505N-0 culture prepared in "3. Thawing of donor lymphocyte".

The patient derived cell suspension is infused into the culture bag with a syringe (e.g., 20 ml syringe with an 18 G injection needle). The culture bag is sealed using a tube sealer. In one example, the total amount of liquid in the culture bag is about 1000 mL.

Cells are cultured, for example, for 1 week in a 37° C. incubator.

5-1. Medium Exchange (e.g., Performed on Week 1, Preferably Under Aseptic Conditions)

In one embodiment, a medium can be exchanged in the following manner. Various numerical values, reagents, procedures, and the exemplified below are like representative examples. Those skilled in the art can exchange a medium while making appropriate changes.

A culture bag is taken out of an incubator. The content is dispensed in a centrifuge tube (e.g., four 225 mL centrifuge tubes).

For example, the content is centrifuged at 600 G for 10 minutes at 22° C. (e.g., preferably, acceleration of the centrifuge can be set to fast, and brake can be set to fast).

The supernatant is gently discarded. A cell pellet is suspended, for example, by adding an ALYS505N-0 culture to prepare a cell suspension (e.g., add ALYS505N-0 culture until reaching a total of 20 mL). At this time, about 0.3 mL of cell suspension is withdrawn to find the cell count and the viable cell count.

For example, to the culture bag containing ALyS505N-0 culture, the cell suspension is added by injection with a syringe (e.g., 20 ml syringe with an 18 G injection needle).

Each of an anti-human CD80 antibody (e.g., 2D10.4) diluent and anti-human CD86 antibody (e.g., IT2.2) diluent is added to the culture bag by injection with a syringe (e.g., 20 mL syringe with an 18 G injection needle) so that the final concentration would each be for example 10 µg/mL (or an inhibitory factor such as a CTLA4-Ig fusion protein (e.g., belatacept) can be used)

5-2. Donor Lymphocyte Thawing/Antigen Restimulation to Start of Secondary Culture (e.g., Performed on Week 1, Preferably Under Aseptic Conditions)

In one embodiment, donor lymphocyte thawing/antigen restimulation to start of secondary culture can be performed in the following manner. Various numerical values, reagents, procedures, and the like exemplified below are representative examples. Those skilled in the art can perform donor lymphocyte thawing/antigen restimulation to start of secondary culture while making appropriate changes.

A preserved donor cell freezing bag and patient derived inactivated plasma are thawed, for example, in a 37° C. thermostatic vessel. The following steps are preferably performed under aseptic conditions.

Donor cell suspension is withdrawn from the thawed freezing bag using a syringe (e.g., 50 ml syringe with an 18 G injection needle) and transferred to a centrifuge tube (e.g., two 50 mL centrifuge tubes).

A 5% albumin solution (e.g., total of about 50 mL for two 50 mL centrifuge tubes) to the centrifuge tube containing the donor cell suspension and thoroughly admixed. The suspension is then incubated for about 5 minutes.

For example, the suspension is centrifuged at 600 G for 10 minutes at 22° C. (acceleration of the centrifuge is set to fast, and brake is set to slow).

The supernatant is gently discarded. A cell pellet is suspended by adding albumin added saline for washing (e.g., prepared from 25 mL of 5% albumin solution and 19 mL of saline).

For example, the cell suspension is centrifuged at 600 G for 10 minutes at 22° C. (acceleration of the centrifuge is set to fast, and brake is set to slow).

The supernatant is gently discarded. A cell pellet is suspended by adding, for example, an ALyS505N culture (e.g., 10 mL to 50 mL centrifuge tube).

The thawed patient derived inactivated plasma (e.g., 10 mL) is added to the culture bag containing an inhibitory factor such as an antibody and a patient cell in the ALYS505N-0 culture prepared in "3. Thawing of donor lymphocyte" by injection with a syringe (e.g., 20 mL syringe with an 18 G injection needle). Furthermore, the cell suspension described above is added to the culture bag by injection with a syringe (e.g., 20 mL syringe with an 18 G injection needle). In one example, the total amount of liquid in the culture bag is about 1000 mL.

The culture bag is sealed using a tube sealer.

The cells are cultured, for example, for 1 week in a 37° C. incubator.

6. Testing During Secondary Culture (Cultured Cell Withdrawal Test)

In one embodiment, testing during secondary culture can be performed in the following manner. Various numerical values, reagents, procedures, and the like exemplified below are representative examples. Those skilled in the art can perform testing during secondary culture while making appropriate changes.

Typically, a small amount of culture is withdrawn from a culture bag and tested for mycoplasma contamination or the like on day 3 from the start of the secondary culture (day 10 of culture).

7. Collection/Loading of Cultured Lymphocyte (Performed Under Aseptic Conditions)

In one embodiment, collection/loading of cultured lymphocyte can be performed in the following manner. Various numerical values, reagents, procedures, and the like exemplified below are representative examples. Those skilled in the art can perform collection/loading of cultured lymphocyte while making appropriate changes.

For example, a culture bag is removed from an incubator on day 7 from the start of the secondary culture (day 14 of culture), and the content is dispensed into a centrifuge tube (e.g., four 225 mL centrifuge tubes).

For example, the content is centrifuged at 600 G for 10 minutes at 22° C. (acceleration of the centrifuge can be set to fast, and brake can be set to fast).

The supernatant is gently discarded. A cell pellet is suspended by adding saline.

For example, the suspension is centrifuged at 600 G for 10 minutes at 22° C. (e.g., preferably, acceleration of the centrifuge can be set to fast, and brake can be set to fast).

The supernatant is gently discarded. A cell pellet is suspended by adding saline (e.g., 10 mL) to prepare a cell suspension.

The cell suspension is gently placed in a centrifuge tube (e.g., 50 mL centrifuge tube) containing a suitable amount of Ficoll-Paque (e.g., 20 mL) as a layer.

For example, the cell suspension is centrifuged at 860 G for 20 minutes at 22° C. (acceleration of the centrifuge is set to slow, and brake is set to slow).

The supernatant is discarded, and the cell suspension comprising a lymphocyte layer is transferred to another centrifuge tube (e.g., 50 mL centrifuge tube).

Saline is added to the centrifuge tube containing the cell suspension (e.g., suitable amount until the total amount of liquid reaches 50 mL). Aspiration and discharge are repeated with a syringe (e.g., 50 mL syringe with an 18 G injection needle) for thorough admixing.

For example, the cell suspension is centrifuged at 500 G for 10 minutes at 22° C. (acceleration of the centrifuge can be set to fast, and brake can be set to fast).

The supernatant is discarded except for about 5 mL. Aspiration and discharge are repeated with a pipette for thorough admixing.

Saline is added (e.g., suitable amount until the total amount of liquid reaches 50 mL). Aspiration and discharge are repeated with a syringe (e.g., 50 mL syringe with an 18 G injection needle) for thorough admixing (a).

For example, the suspension is centrifuged at 500 G for 5 minutes at 22° C. (acceleration of the centrifuge can be set to fast, and brake can be set to fast) (b).

The supernatant is discarded except for about 5 mL. Aspiration and discharge are repeated with a pipette for thorough admixing (c).

(a), (b), and (c) are repeated two more times.

A suitable amount of the supernatant after the final centrifugation is withdrawn (e.g., 4 mL) and subjected to a sterility test and mycoplasma test.

The cells are suspended by adding saline again. The cell suspension is transferred to the final container (e.g., 100 mL saline bottle). A suitable amount (e.g., 4 mL) is withdrawn. The cell count, viable cell count, expression of a surface antigen, and endotoxin content of the final product are studied.

8. Secondary Packaging

In one embodiment, secondary packaging can be performed in the following manner. Various numerical values, reagents, procedures, and the like exemplified below are representative examples. Those skilled in the art can perform secondary packaging while making appropriate changes.

Typically, a subject ID, manufacture number, and expiration date are entered and printed on a label based on a suitable standard (typically NUHCPC-M-12-ATREG) and the label is applied to a container.

"Dosage and Administration, indication, and precaution for use or handling" is specified based on a suitable standard (typically NUHCPC-PMF-ATREG14).

The tested material and "Dosage and Administration, indication, and precaution for use or handling" are placed in a resealable plastic bag.

The bag is stored within a monitoring unit in a transport container until shipping.

(Note)

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present disclosure has been described while showing preferred embodiments to facilitate understanding. While the present disclosure is described hereinafter based on the Examples, the above descriptions and the following Examples are provided for the sole purpose of exemplification, not limitation of the present disclosure. Thus, the scope of the present disclosure is not limited to the embodiments and Examples that are specifically described herein and is limited only by the scope of claims.

EXAMPLES

The present disclosure is more specifically described hereinafter based on the Examples. However, the present disclosure is not limited to the Examples. Throughout the entire application, all of the cited references are directly incorporated herein by reference.

Example 1: Loss of Function Assay

This Example conducted a loss of function assay to identify a component that is required for eliciting immune tolerance. This is described hereinafter.

Materials and Methods (Production of Anergic Cells)

The experiment was conducted in accordance with a method already described in a reference (1-3). Briefly, spleens were extracted from C57BL6 (hereinafter B6) mice and BALB/c mice (Clea Japan, Charles River Laboratories Japan, etc.), and red blood cells were subjected to hemolysis to obtain splenocytes (lymphocytes), which were then adjusted in an RPMI 1640 medium (Sigma; R8758-500MK) comprising 10% inactivated fetal calf serum (FCS) (SIGMA #172012-500ML Lot 11D257 or biosera #FB-1380/500 Lot. 015BS482) so that the concentration would be $4\times10^6$ cells/ml. The stimulator BALB/c splenocytes were irradiated with 30 Gy of radiation (γ ray) and then mixed with B6 splenocytes at 1:1. The cells were cultured for 14 days in a 37° C. 5% $CO_2$ incubator in a 12-well plate (Corning, #3513) (1 to 2.5 mL), 6-well plate (Corning, Cat. No. 3516) (3 to 6 mL), 6 cm Petri dish (Greiner CELLSTAR® dish, Cat. No. 628160) (3 to 6 mL), or 10 cm petri dish (Corning, Cat. No. 430167) (10 to 15 mL) after adding eBioscience's hamster anti-mouse CD80 antibody (16-10A1) (Cat. No. 16-0801-82) and rat anti-mouse CD86 antibody (GL1) (Cat. No. 14-0862-82) so that each final concentration would be 10 µg/mL. After removing the culture by centrifugation on day 7 from the start of the culture, a culture comprising a BALB/c derived radiation irradiated splenocyte and anti-CD80 antibodies/anti-CD86 antibodies was newly added under the same condition as that at the start of culture. After 14 days, cells were collected to obtain anergic cells.

In some experiments, a PE fluorescence labeled anti-mouse CD8 antibody (53-6.7; eBioscience, #12-0081-85) was reacted with the anergic cell, and cells were sorted into CD8 positive and CD8 negative with auto-MACS (Miltenyi Biotec) using anti-PE magnetic beads (Miltenyi Biotec #1300-10-639). The same operation was also performed using a PE fluorescence labeled CD19 antibody (1D3; eBioscience, #12-0193-85) to sort the cells into CD19 positive and CD19 negative. These cells were used in an immune response suppressing ability test. In some experiments, B6 derived mice (4) were used, which were genetically modified in a manner that a responder cell concurrently expresses FoxP3 and human CD2 so that a FOXP3 expressing regulatory T cell (reg T cell) can be identified by the expression of a cell surface antigen to sort cells into human CD2 positive cells (FoxP3 expressing reg T cell) and human CD2 negative cells with auto-MACS using anti-PE magnetic beads and a PE fluorescence labeled anti-human CD2 antibody (RPA-2.10; eBioscience, #12-0029-42), and the cells were used in an immune response suppressing ability test.

(Evaluation of Immune Response Suppressing Ability)

An experiment was conducted in accordance with a method already described in a reference (3). Briefly, anergic cells were adjusted so that the ratio with respect to responder B6 splenocytes would be ½ to ¹⁄₁₆. The anergic cells were then added to a 1:1 mixed culture (ultimately 4 well each at 200 µL/well) at $1\times10^6$ cells/mL using newly harvested B6 mouse and BALB/c mouse splenocytes on a 96-well plate (Corning, Cat. No. 3799) and cultured in a 37° C. 5% $CO_2$ incubator (the cell count of each of B6 mouse and BALB/c mouse splenocytes was $1\times10^5$ cells, and the cell count of the anergic cells was ½ to ¹⁄₁₆ of $1\times10^5$ cells per well). On day 4 from the start of the culture, 3H-thymidine (10 µL) was added. On day 5 from the start of the culture (after 16 to 20 hours from addition of 3H-thymidine), cultured cells were harvested with a Cell Harvester (Molecular Devices). The amount of 3H-thymidine incorporation was measured with a scintillation counter. The graphs were prepared based on the amount of 3H-thymidine incorporation of a naïve B6 lymphocyte without stimulation being 1 for a comparative study.

Results

Figure 1A:
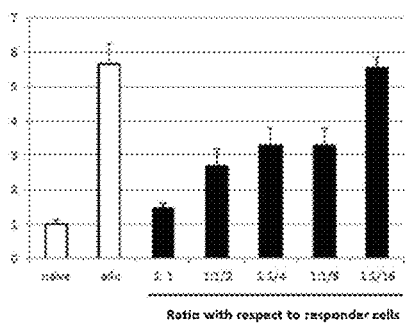
FIG. 1 shows results of a loss of function assay for identifying a component required for eliciting immune tolerance. (i) Production of anergic cells: Spleens were extracted from C57BL6 (hereinafter, abbreviated as B6) mice and BALB/c mice to obtain splenocytes (lymphocytes). The stimulator BALB/c splenocytes were then irradiated with 30 Gy of radiation (γ ray), and then mixed with B6 derived splenocytes at 1:1. Anti-CD80 and anti-CD86 antibodies were added so that the final concentration of each would be 10 µg/mL. Culture was started in a 37° C. 5% $CO_2$ incubator in a culture of a suitable volume. After removing the culture by centrifugation on day 7 from the start of the culture, a culture comprising BALB/c derived radiation irradiated splenocytes and anti-CD80 antibodies/anti-CD86 antibodies were newly added under the same condition as the start of culture. On day 14 of the culture, cells were retrieved, and anergic cells were obtained. (ii) Sorting each cellular phenotype: The resulting anergic cells were reacted with a PE fluorescence labeled anti-CD8 antibody, and cells were sorted into CD8 positive and CD8 negative with an automatic magnetic cell separator (auto-MACS) using anti-PE magnetic beads. The same operation was performed using a PE fluorescence labeled CD19 antibody to sort cells into CD19 positive and CD19 negative. Furthermore, human CD2 positive cells (FoxP3 expressing reg T cells) were sorted from human CD2 negative cells with auto-MACS using PE fluorescence labeled anti-human CD2 antibodies and anti-PE magnetic beads by using B6 derived mice that were genetically engineered in a manner that a responder cell concurrently expresses FoxP3 and human CD2 so that FOXP3 expressing regulatory T cells (reg T cells) can be identified from the expression of a cell surface antigen. The cells were used in an immune response suppressing ability test. (iii) Immune response suppressing ability test: Newly harvested B6 mouse derived splenocytes were used as responders, and newly harvested BALB/c mouse splenocytes were used as stimulators. A mixed culture comprising each cell at a ratio of 1:1 was prepared at a volume of 200 μL in each well of a 96-well plate (cell count per well was $1×10^5$ cells for each cell). To the mixed culture, all anergic cells without any sorting (FIG. 1a), cell population of only anergic CD8 positive cells or remaining cell population after excluding anergic CD8 positive cells (FIG. 1b), cell population of only reg T cells or remaining cell population after excluding reg T cells (FIG. 1c), or cell population of only CD19 positive cells (B cells) or remaining cell population after removing B cells (FIG. 1d) was added so that the ratio of cell count to that of responder B6 splenocytes would be 1, ½, ¼, ⅛, or 1/16, and cultured in a 37° C. 5% $CO_2$ incubator. On day 4 from the start of the culture, 3H-thymidine was added. On day 5 from the start of the culture (16 to 20 hours after adding the 3H-thymidine), cultured cells were collected, and the amount of 3H-thymidine incorporation was measured with a scintillation counter. In each diagram, "naive" is a well of only responders, and "allo" is a well of only responders and stimulators. The graphs were prepared based on the mean value of the amount of 3H-thymidine incorporation of "naive" being 1.

The results are shown in FIG. 1. The values indicate values calculated based on the mean value of the amount of 3H-thymidine incorporation in an unstimulated state (naïve)

being 1. As shown in FIG. 1a, all cultured B6 splenocytes without any sorting were confirmed to have an effect of suppressing a response to BALB/c splenocytes of fresh (naïve) B6 splenocytes, after being cultured with stimulator BALB/c splenocytes in the presence of anti-CD80/86 antibodies (hereinafter, referred as to "antibody/stimulator treatment"). The energy induced all cultured cells (cell mixture) are also expected to comprise other cells (CD19 positive B cell) in addition to an anergic CD8 positive cell, an anergic CD4 positive cell, and a regulatory T cell (reg T cell).

Figure 1B:
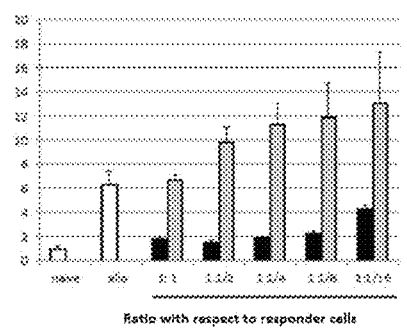

When an experiment was conducted using a sample prepared from purifying CD8 positive cells (most are CD44 positive anergic CD8 positive cells) from a cell mixture after the antibody/stimulator treatment, it was found that there is also an effect of suppression in a cell population of only anergic CD8 positive cells (black). It was shown that the rest of the cell population excluding the anergic CD8 positive cells did not have a suppressive effect (gray) (FIG. 1b).

Figure 1C:
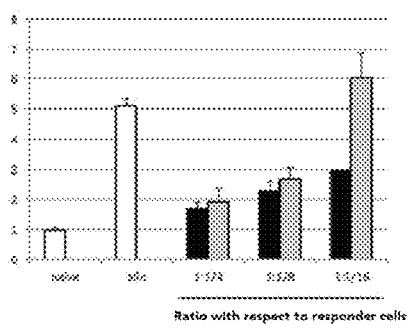

As shown in FIG. 1c, it was demonstrated that when human CD2 positive cells=reg T cells were purified from a cell mixture after antibody/stimulator treatment, there was a suppression effect even in a cell population of only reg T cells (black), and the rest of the cell population excluding the reg T cells had the same suppression effect (grey).

Figure 1D:
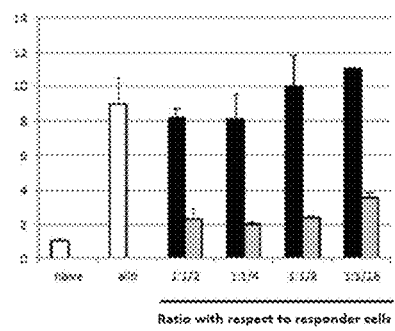

Meanwhile, as shown in FIG. 1d, it was demonstrated that when CD19 positive cells (B cells) were purified from a cell mixture after the antibody/stimulator treatment, there is no suppression effect in a cell population of only B cells (black), but there is a suppression effect in the rest of the cell population excluding the B cells (grey).

In this manner, elimination of CD8 positive cells significantly reduces suppression of immune responses=induction of immune tolerance, and a potent immune tolerance induction was exhibited with CD8 positive cells alone. Thus, it is understood that CD8 positive cells are cells that are essential for the induction of effective immune tolerance. Therefore, it is understood that confirming the presence/absence of CD8 positive cells is important for quality control when manufacturing an immune tolerance induced cell product.

The same suppression action was also observed in a purified FOXP3 positive cell population and a FOXP3 positive cell lacking cell population. This is not inconsistent with CD8 positive cells having the ability to induce immune tolerance. This is also consistent with FOXP3 positive cells, which are widely known as regulatory T cells, having an immunosuppressive ability. Therefore, it is understood that cells which are effective in inducing immune tolerance among all anergic cells after antibody/stimulator treatment are anergic CD8 positive cells and FOXP3 positive cells, and a mixture thereof induces immune tolerance most effectively.

It was found from an experiment sorting by CD19 that CD19 positive cells (B cells) do not have a suppression effect. It is understood that a CD19 positive cell is not required.

Example 2: Acquisition of Suppression Function Assay by CD80/86 Blocking

This Example confirmed that the ability to induce immune tolerance (rejection suppression ability) of CD8 positive T cells is due to induction of anergy by antibody/stimulator treatment. The same experiment was also conducted for FOXP3 positive T cells.

Materials and Methods

Anergic cells were obtained by applying antibody/stimulator treatment on splenocytes obtained from wild type B6 mice and B6 derived mice that were genetically modified to concurrently express FoxP3 and human CD2 by the same approach as Example 1. The anergic cells and unstimulated naïve splenocytes obtained from wild type B6 mice and B6 derived mice that were genetically modified to concurrently express FoxP3 and human CD2 were reacted with a PE fluorescence labeled anti-mouse CD8 antibody or PE fluorescence labeled anti-human CD2 antibody. The cells were then sorted into CD8 positive and CD8 negative, or human CD2 positive and human CD2 negative by auto-MACS using anti-PE magnetic beads. Each of the sorted cells was added to a mixed culture system on a 96-well plate to study the immunosuppressive ability thereof.

Results

The results are shown in FIG. 2.

Figure 2A:
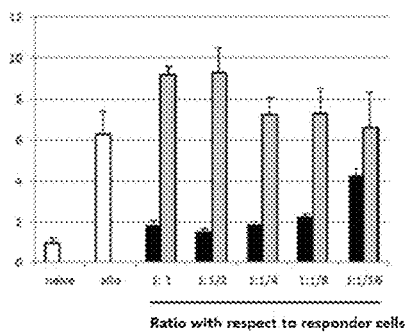
FIG. 2 shows an acquisition of suppression function assay by CD80/86 blocking. Anergic cells were obtained by treating splenocytes obtained from wild-type B6 mice and B6 derived mice that were genetically engineered to concurrently express FoxP3 and human CD2 with BALB/c derived radiation irradiated splenocytes and anti-CD80 antibodies/anti-CD86 antibodies by the same approach as Example 1. The anergic cells, together with unstimulated naïve splenocytes obtained from wild-type B6 mice and B6 derived mice that were genetically engineered to concurrently express FoxP3 and human CD2, were reacted with a PE fluorescence labeled anti-mouse CD8 antibody or PE fluorescence labeled anti-human CD2 antibody. The cells were then sorted into CD8 positive and CD8 negative, or human CD2 positive and human CD2 negative through auto-MACS using anti-PE magnetic beads. Each of the sorted cells was added to the mixed culture system on a 96-well plate described in Example 1, and the immunosuppressive ability thereof was studied. In each diagram, "naive" (more specifically, ï represents diaeresis (two dots on top); the same applies hereinafter) is a well of only responders, and "allo" is a well of only responders and stimulators. The graphs were prepared based on the mean value of the amount of 3H-thymidine incorporation of "naive" being 1.
Figure 2B:
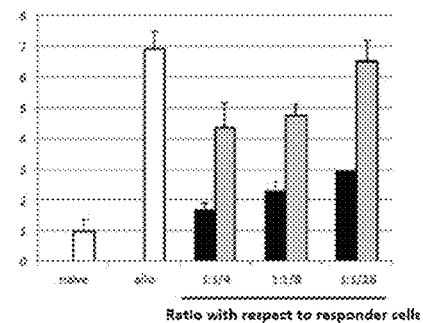

As shown in FIG. 2a (the values indicate values calculated based on the mean value of the amount of 3H-thymidine incorporation in an unstimulated state (naïve) being 1), it was demonstrated that anergic CD8 positive cells have a suppression effect (black), and CD8 positive cells isolated from unstimulated naïve splenocytes do not have a suppression effect (grey). As shown in FIG. 2b, it was demonstrated that reg T cells after antibody/stimulator treatment (black) also exert an immunosuppressive ability, which is stronger than that of unstimulated naïve reg T cells (grey).

It was found in view of the above that elicitation of immune tolerance (suppression of immune responses) by a CD8 positive cell requires induction of anergy by stimulation using a stimulator BALB/c splenocyte in the presence of anti-CD80/86 antibodies, and the same applies to reg T cells for exerting a more potent immune suppressive function. Specifically, anergic CD8 positive cells and reg T cells induced by antibody/stimulator treatment were demonstrated to have a potent ability to induce immune tolerance. (Example 3: Ability to induce tolerance after transplantation of purified anergic cell)

This Examples studied whether a purified cell after induction of anergy had an ability to induce tolerance after transplantation.

Materials and Methods

Anergic cells were obtained from splenocytes of wild type B6 mice and B6 derived mice that were genetically modified to concurrently express FoxP3 and human CD2 by co-culturing with stimulator BALB/c splenocytes in the presence of anti-CD80/86 antibodies by the same approach as Example 1. In some experiments, the resulting anergic cells (all anergy cells) were sorted into CD8 positive cells, CD4 positive cells, or human CD2 positive cells by the same approach as Example 1. The hearts of BALB/c mice were transplanted 3 days after irradiation with 2 Gy of radiation (γ ray) to wild type B6 mice. Naïve B6 splenocytes or obtained anergic cells were administered immediately thereafter (or on the same day as the heart transplant) from the caudal vein, and the rejection of the hearts was observed. The experiments were conducted with 5 or more mice for each group.

Results

Figure 3:
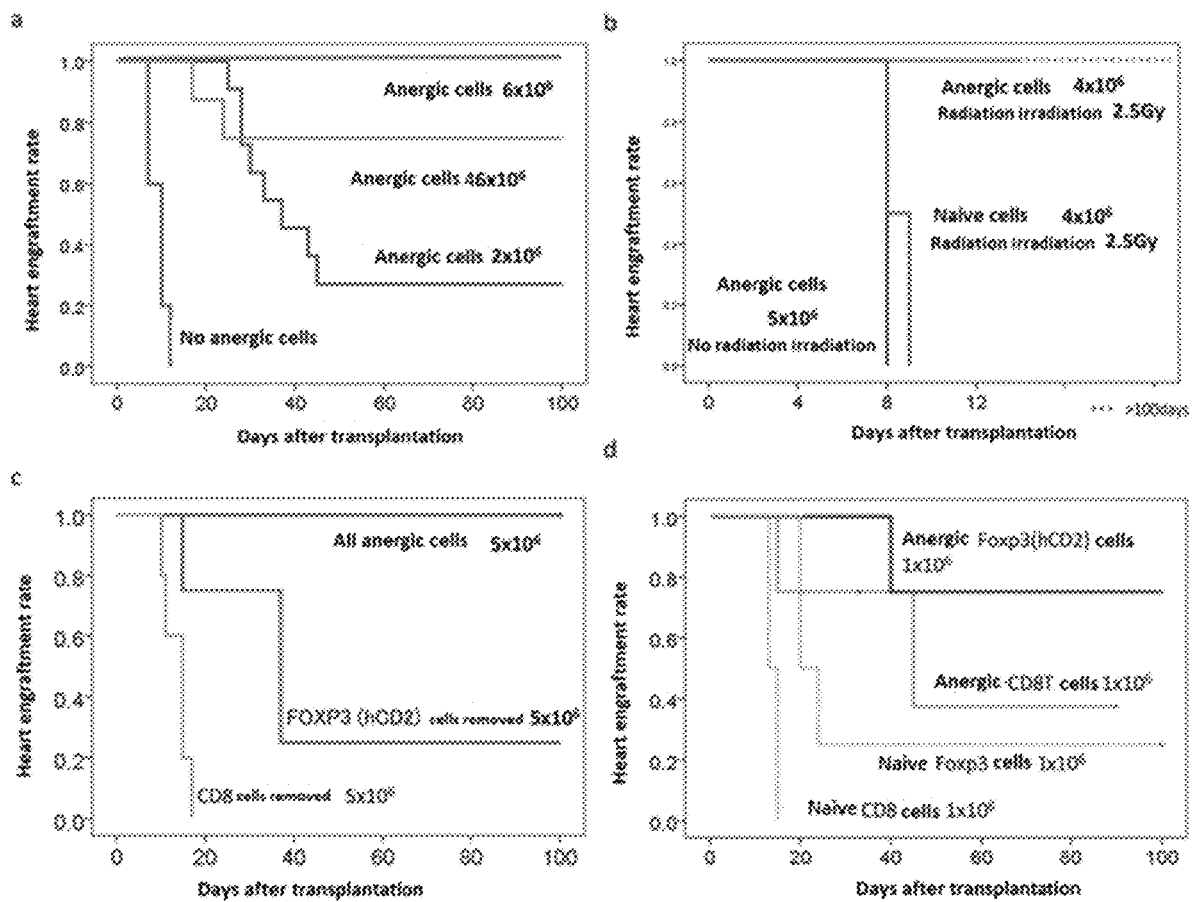
FIG. 3 shows results of testing whether purified cells after induction of anergy have the ability to induce tolerance after transplantation in an experiment using mice. Anergic cells were obtained by treating splenocytes obtained from wild-type B6 mice and B6 derived mice that were genetically engineered to concurrently express FoxP3 and human CD2 with BALB/c derived radiation irradiated splenocytes and anti-CD80/anti-CD86 antibodies by the same approach as Example 1. CD8 positive cells, CD4 positive cells, or human CD2 positive cells were sorted out from the obtained anergic cells (all anergic cells) by the same approach as Example 1. The hearts of BALB/c mice were transplanted 3 days after irradiating 2 Gy of radiation (γ ray) on a wild-type B6 mouse. Immediately thereafter (or on the same day as the heart transplant), naïve B6 splenocytes or the obtained anergic cells were administered to the caudal vein to observe rejection of the heart. The experiment was conducted with 5 or more mice in each group.

FIG. 3 shows the results thereof. As shown in FIG. 3a, the transplanted heart was rejected by about 2 weeks in all cases if anergic cells were not transplanted. In contrast, the engraftment rate of the heart was improved depending on the administered cell count in all anergy cell administration groups. For transfusion of 6×10⁶ all anergic cells, the hearts transplanted into mice all survived even after 100 days, from which it is deemed that tolerance to the transplanted heart is induced. As shown in FIG. 3b, the induction of tolerance was observed only when anergic cells were infused after irradiation of radiation into a recipient mouse. This was not observed at all when anergic cells were administered without irradiation of radiation or when naïve cells were infused into a radiation irradiated mouse. When a cell population obtained from removing human CD2 positive cells (FoxP3 expressing reg T cells) or anergic CD8 positive cells from anergic cells was administered to a radiation irradiated mouse, engraftment was not observed after 100 days in the same manner as all anergic cell infusion in 100% of transplanted hearts, and the ability to induce tolerance was clearly diminished. Thus, superiority of administration of all anergic cells (anergic cell mixture) was apparent (FIG. 3c). When purified naïve CD8 positive T cells were administered, the hearts transplanted into mice were all rejected, but when anergic CD8 positive T cells were infused, tolerance was induced in 40% of administered mice (FIG. 3d). Furthermore, tolerance was induced in some mice when naïve human CD2 positive cells (FoxP3 expressing reg T cells) were infused, but tolerance was induced more efficiently with administration of anergic human CD2 positive cells (FoxP3 expressing reg T cells) (FIG. 3d). Therefore, administration of an anergic cell mixture was shown to induce tolerance more efficiently than individual administration of each of anergic CD8, CD4, and FoXP3 positive cells by more efficiently suppressing rejection for the transplanted heart and by bringing out myelosuppression from irradiation of radiation on the recipient or the like.

This result is not inconsistent with Example 1. The result does not negate the possibility of individual administration of purified anergic CD8, CD4, FoxP3 positive cells or naïve FoXP3 positive cells exhibiting suppression of rejection of the transplanted heart (induction of tolerance=survival of the transplanted heart of 100 days or more) similar to the infusion of an anergic cell mixture if the number of cells is high. In this experiment, genetically engineering mice were used, so that Foxp3 expressing cells=suppressor T cells were able to be purified alive with the expression of human CD2 on the cell surface, but Foxp3 expression in cells generally cannot be detected in live cells. It is known that when CD25 positive CD4 positive T cells are used instead, more activated CD4 positive T cells are contained than suppressor T cells, and the immunosuppression function thereof is weak. Since there are fewer Foxp3 positive suppressor T cells, purification of anergic Foxp3 expressing suppressor cells is very difficult. In fact, 1×10⁷ or more all anergic cells were required to obtain 1×10⁶ human CD2 expressing cells=FoxP3 expressing cells shown in FIG. 3d. Therefore, the result shown in this Example clearly indicates that a mixture is more practical and effective.

Example 4: Ability of Human PBMC Derived Anergic Cell

This Example evaluated the ability of human PBMC derived anergic cells.

Materials and Methods (Production of Anergic Cells)
The experiment was conducted in accordance with a method already described in a reference (5-8). Mononuclear cells (PBMC) were separated from human peripheral blood of 4 volunteers (2 were designated as stimulators and 2 were designated as responders) using Promo cell's Lymphocyte separation Media (Cat. No. C-44010), Ficoll-Paque PREMIUM (GE Healthcare #17-5442-02), Lymphocyte separation Solution (Nacalai Tesque #20828), or the like, and adjusted with a 2% human type AB serum (pooled) added Biowest ALYS505N-0 medium (Cell Science & Technology Institute (CSTI) 1020P10) so that the concentration would be 4×10⁶ cells/ml. Stimulator PBMCs were irradiated with 30 Gy radiation (γ ray) and mixed with responder PBMCs at 1:1. To the mixed PBMCs, eBioscience's mouse anti-human CD80 antibodies (2D10.4) (Cat. No. 16-0809-85) and mouse anti-human CD86 antibodies (IT2.2) (Cat. No. 16-0869-85) were added so that the final concentration would each be 10 μg/mL, and culture was started in a 37° C. 5% CO₂ incubator on a 12-well plate (Corning, #3513), 6-well plate (Corning, Cat. No. 3516), 6 cm petri dish (Greiner CELLSTAR® dish, Cat. No. 628160), or 10 cm petri dish (Corning, Cat. No. 430167). After removing the culture by centrifugation on day 7 from the start of the culture, a culture comprising anti-CD80 antibodies/anti-CD86 antibodies and radiation irradiated stimulator PBMCs were added under the same condition as the start of the culture. On day 14, the cells were collected, and the culture was washed out by centrifugation to obtain anergic cells. In some experiments, anergic cells were stained with a PE fluorescence labeled mouse anti-human CD25 antibody (BC96; eBioscience #12-0259-42), FITC fluorescence labeled mouse anti-human CD4 antibody (RPA-T4; eBioscience #11-0049-42), or APC fluorescence labeled mouse anti-human CD8 antibody (RPA-T8; eBioscience #17-0088-42), and each cell was then purified using a JSAN cell sorter (Bay bioscience Co., Ltd.) and added to the mixed culture system.

(Evaluation of Ability to Suppress Immune Responses)
After adjusting the obtained anergic cells so that the ratio with respect to responder PBMCs would be ½ to ¹⁄₁₆, the cells were added to a mixed culture system of 4 wells each at 2×10⁵ cells/200 L/well on a 96-well plate (Corning, Cat. No. 3799) using newly harvested PBMCs of the same volunteer and cultured in a 37° C. 5% CO₂ incubator. On day 4 from the start of the culture, 3H-thymidine (10 μL) was added. On day 5 from the start of the culture (after 16 to 20 hours from addition of 3H-thymidine), cultured cells were harvested with a Cell Harvester (Molecular Devices). The amount of 3H-thymidine incorporation was measured with a scintillation counter. The graphs were prepared based on the amount of 3H-thymidine incorporation of a naïve responder PBMC without stimulation being 1 for a comparative study.

Results

Figure 4A:
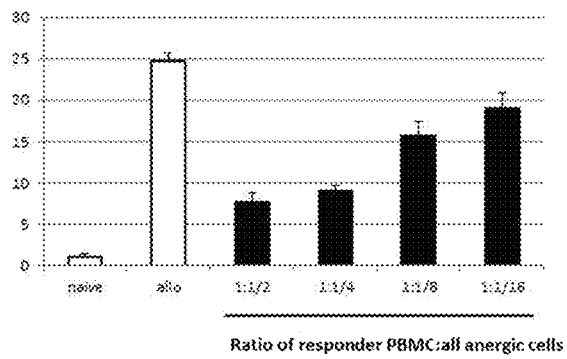
FIG. 4 shows the ability of human PBMC derived anergic cells. (i) Production of anergic cells: Mononuclear cells (PBMC) were separated from human peripheral blood of 4 volunteers (2 are designated as stimulators, and 2 are designated as responders). Stimulator PBMCs were irradiated with 30 Gy of radiation (γ ray) and mixed with responder cells at 1:1. Anti-human CD80 antibodies and anti-human CD86 antibodies were added to the mixed PBMCs so that the final concentrations thereof were each 10 μg/mL. Culture was started in a 37° C. 5% $CO_2$ incubator in a culture of a suitable volume. After removing the culture by centrifugation on day 7 from the start of the culture, a culture comprising anti-CD80 antibodies/anti-CD86 antibodies and radiation irradiated stimulator PBMCs was added under the same condition as the start of the culture. On day 14, the cells were collected, and the culture was washed out by centrifugation to obtain anergic cells. (ii) Sorting of each cellular phenotype: the obtained anergic cells were stained with a PE fluorescence labeled mouse anti-human CD25 antibody, FITC fluorescence labeled mouse anti-human CD4 antibody, or APC fluorescence labeled mouse anti-human CD8 antibody, then each cell was purified using a JSAN cell sorter (Bay bioscience Co., Ltd.). (iii) Immune response suppressing ability test: Newly collected PBMCs of the same volunteer were used as responder and stimulator. A mixed culture comprising each cell at a ratio of 1:1 was prepared in each well of 96-well plate at a volume of 200 μL (cell count per well was $2×10^5$ cells for each cell). All anergic cells were added to the mixed culture so that the ratio to the cell count of responder PBMCs would be ½, ¼, ⅛, or 1/16, and cultured in a 37° C. 5% $CO_2$ incubator (FIG. 4a).
In FIG. 4b, a CD25 positive cell purified cell population (CD25+), CD4 positive CD25 positive reg T cell purified cell population (CD4+CD25+), or purified CD4 positive CD25 positive reg T cell and purified CD8 positive cell added cell population (CD25+/CD8+) were added to the mixed culture so that the ratio to the cell count of responder PBMCs would each be ½.
In FIG. 4c, a CD4 positive cell purified cell population, CD4 negative cell purified cell population, or all anergic cells were added to the mixed culture so that the ratio to the cell count of responder PBMCs would be ½, ¼, ⅛, or 1/16, and the immunosuppression abilities were compared. In each diagram, "naive" is a well of only responders, and "allo" is a well of only responders and stimulators. The graphs were prepared based on the mean value of the amount of 3H-thymidine incorporation of "naive" being 1.
Figure 4B:
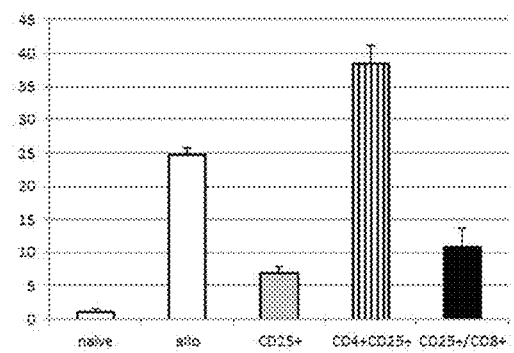

The results are shown in FIG. 4.
FIG. 4a shows the dose dependent ability to suppress immune responses of "all anergic cells after antibody/stimulator treatment". It is clear that the suppression effect is higher for a higher ratio of all anergic cells after antibody/stimulator treatment.
FIG. 4b compares the immunosuppression ability using, from the third bar from the left to the right in order, a cell population obtained from purifying CD25 positive cells comprising CD8 positive CD44 positive anergic cells and reg T cells (gray), cell population obtained from purifying CD4 positive CD25 positive reg T cells (vertical stripes), and cell population obtained from adding purified CD8 positive cells to purified CD4 positive CD25 positive reg T cells (black), by sorting all anergic cells after antibody/stimulator treatment. It is clear from the results shown therein reg that T cells alone have no immunosuppression ability and exert an immunosuppression ability by coexisting with CD8 positive T cells.

Figure 4C:
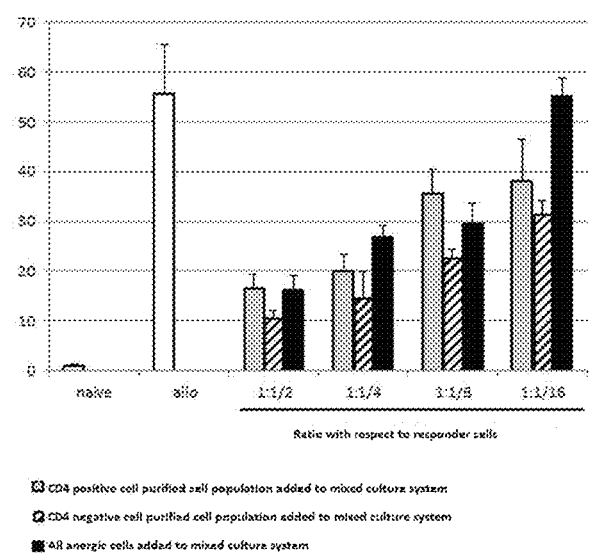

FIG. 4c sorted all anergic cells after antibody/stimulator treatment into CD4 positive cells (gray) and CD4 negative cells (diagonal lines) and compared the immunosuppression ability with all anergic cells (black). The values indicate values calculated based on the mean value of the amount of 3H-thymidine incorporation in an (naïve) being 1. CD4 positive cells unstimulated state include reg T cells, and CD4 negative cells include CD8 positive cells. Immunosuppression is exhibited in CD4 positive cells and CD4 negative cells.

FIG. 4b suggests that exertion of sufficient immunosuppression ability of reg T cells requires the presence of CD4 positive cells other than CD8 positive cells or reg T cells, because reg T cells alone could not exert an immunosuppression ability, and reg T cells exerted an immunosuppression ability in the presence of a CD8 positive cell. It is understood that the immunosuppression ability of CD4 negative cells is from anergic CD8 positive T cells contained therein.

Example 5: Experiment Showing Antigen Specific Suppression

This experiment studied donor specific tolerance induction of all anergic cells after antibody/stimulator treatment.

Materials and Methods

Anergic cells were obtained by stimulating splenocytes obtained from wild-type B6 mice (H-$2^b$) with splenocytes derived from BALB/c mice (H-$2^b$) in the presence of anti-CD80/86 antibodies and culturing the splenocytes by the same approach as Example 1.5×$10^6$ anergic cells were administered to wild-type B6 mice transplanted with a heart of a BALB/c mouse or CBA mouse (H-$2^k$) three days after irradiation of 2 Gy of radiation from the caudal vein to observe rejection of the heart.

Result

Figure 5:
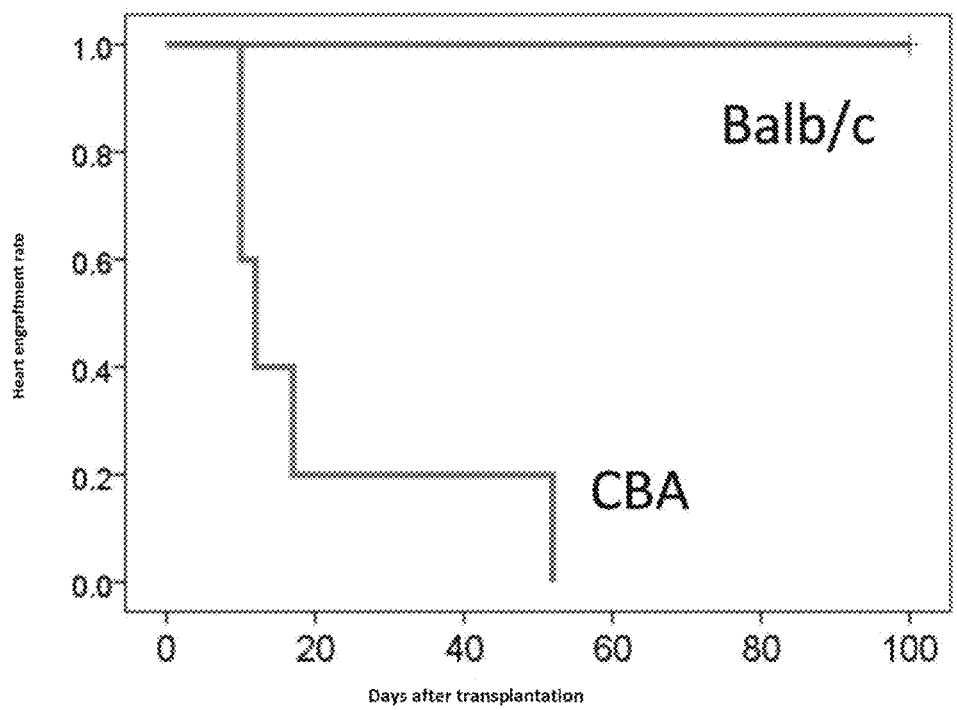
FIG. 5 is a diagram showing that immunosuppression by anergic cells is antigen specific. This diagram shows the engraftment rate of hearts after transplant of B6 mouse derived anergic cells stimulated with Balb/C mouse splenocytes in the presence of anti-CD80/86 antibodies into a B6 mouse. It was demonstrated that rejection of the transplanted BALB/c mouse heart was inhibited 100% and the heart was surviving after 100 days, whereas a heterologous (3$^{rd}$ party) CBA mouse heart quickly induced rejection after transplantation, and the heart was rejected 100% at about 50 days.

As shown in FIG. 5, infusion of anergic cells from a B6 mouse stimulated with Balb/C mouse splenocytes in the presence of anti-CD80/86 antibodies into a B6 mouse inhibited rejection of the transplanted heart of the BALB/c mouse 100%. The heart was surviving even after 100 days, i.e., tolerance was induced. In contrast, 3rd party CBA mouse hearts quickly induced rejection after transplantation and were rejected 100% at about 50 days.

This shows that a lymphocyte derived from a host reacted with an antigen in the presence of anti-CD80/86 antibodies has an ability to suppress immune responses specific to this antigen.

Example 6: Suppression of Immune Responses of Naïve Cells by Selective Early Adhesion of Anergic Cells This experiment confirmed that an anergic cell binds to a donor (stimulator) cell more quickly than a naïve cell to inhibit reaction and proliferation of naïve cells.

Materials and Methods

Anergic cells were obtained by stimulating splenocytes obtained from a B6 mouse with splenocytes derived from a BALB/c mouse in the presence of anti-CD80/86 antibodies by the same approach as Example 1. In this experiment, splenocytes newly obtained from a B6 mouse genetically engineered to constantly express fluorescent dye GFP were used as a responder. The anergic cells were added to a 4 ml mixed culture system comprising the aforementioned responder B6 splenocytes and stimulator (donor) BALB/c splenocytes each at 1×$10^6$ cells/ml so that the ratio with respect to the responder B6 splenocytes would be ½ in a 12-well plate (Corning, Cat. No. 3799), and cultured in a 37° C. 5% $CO_2$ incubator. The plate was observed over time from one day after to three days after, and pictures were taken.

Results

FIG. 6 shows representative images of the pictures. A cluster of cells was formed after 1 day of culture only in a culture system added with anergic cells in the bottom row. This is not observed in a system of only naïve cells and donor cells (second row from the top). Therefore, it is inferred that the anergic cells likely formed a cluster of cells mainly of BALB/c derived cells. After two days of culture and thereafter, naïve B6 splenocytes also started to form a cluster of cells. At the same time, fluorescence at the site became more intense. This is understood to be due to an increase in fluorescence emitting naïve cells that adhered to and reacted with BALB/c splenocytes. Such an enhancement in fluorescence was not observed in a culture of naïve cells alone on the top row or a culture system added with anergic cells. Therefore, it is suggested that a proliferation reaction of naïve cells is suppressed by the addition of anergic cells. The results suggest that an anergic cell adheres to a donor cell more quickly than a naïve cell and inhibits recognition (adhesion) of the donor cell by the naïve cell to inhibit the reaction=proliferation of naïve cells.

Example a Exerting 7: Attribute of Cell an Immunosuppression Ability (Anergy Inducing Ability)

This Example conducted an experiment to confirm that cells exerting an immunosuppression ability (anergy inducing ability) among anergic cells are CD44 positive.

Materials and Methods

Anergic cells were obtained by stimulating splenocytes obtained from a wild-type B6 mouse with BALB/c cells in the presence of anti-CD80/86 antibodies by the same approach as Example 1. The anergic cells were stained with APC fluorescence labeled anti-mouse CD8 antibodies (53-6.7; eBioscience #17-0081-82 or BioLegend; #100730), PerCP/Cy5.5 fluorescence labeled anti-mouse CD4 antibodies (RM4-5; eBioscience #45-0042-82 or GK1.5; BioLegend; #100434), and APC/Cy7 fluorescence labeled anti-mouse CD44 antibodies (BioLegend; #1003028), and then added to a mixed culture system after removing CD8 positive CD44 negative cells or CD4 positive CD44 negative cells using a JSAN cell sorter (Bay bioscience Co., Ltd.). An experiment which purified CD8 positive CD44 positive cells or CD4 positive CD44 positive cells using a JSAN cell sorter and added the cells to a mixed culture system was also conducted.

Results

As shown in FIG. 7a, it was observed that cells obtained from removing CD8 positive CD44 negative cells or CD4 positive CD44 negative cells from anergic cells suppress further proliferation of naïve B6 splenocytes which are responder cells in a new mixed culture system in the same manner as addition of all anergic cells. This shows that CD44 negative cells do not have immunosuppressive action, i.e., anergy inducing ability. Furthermore, as shown in FIG. 7b, purified CD8 positive CD44 positive cells or CD4 positive CD44 positive cells also have an immunosuppressive property individually. It was confirmed that immunosuppression by anergic CD8 positive cells or anergic CD4 positive cells shown in the Examples up to this point was exerted by CD44 positive cells.

When the phenotypes of the anergic cells were studied together by FACS, anergic CD44 positive cells with a strong immunosuppressive function were 16.61% among anergic CD8 positive T cells, and anergic CD44 positive cells with a strong immunosuppressive function among anergic CD4 positive T cells were 31.01%, as shown in FIG. 7c.

Example 8: Elicitation of Immune Tolerance Using Various Inhibitory Factors

This Example shows that immune tolerance can also be elicited using various inhibitory factors.
(Production of Anergic Cells)
Basically, experiments are conducted according to the method described in Example 1 and a method already described in a reference (1 to 3). Recipient PBMCs and donor PBMCs freshly separated from human peripheral blood are used, or those cryopreserved at −80° C. that were rapidly thawed are used. These cells are both adjusted to $4\times10^6$ cells/mL in a RPMI 1640 medium (Sigma; R8758-500MK) comprising their own plasma or 10% inactivated fetal bovine serum (FCS) (SIGMA #172012-500ML Lot 11D257 or biosera #FB-1380/500 Lot. 015BS482). Donor PBMCs are irradiated with 20 Gy of radiation. The recipient PBMCs and donor PBMCs are mixed at 1:1. An inhibitory factor (e.g., for each of anti-CD80 antibodies/anti-CD86 antibodies, final concentration of 10 μg/ml; for belatacept (or abatacept), final concentration of 10 μg/ml to 40 μg/ml) is added to the mixture. The mixture is cultured for 7 days in a 37° C. 5% $CO_2$ incubator on a 6 cm petri dish (Greiner CELLSTAR® dish, Cat. No. 628160) (culture volume of 3 to 6 mL) or 10 cm petri dish (Corning, Cat. No. 430167) (culture volume of 10 to 15 mL) (cell density at start of culture is $4\times10^6$ cells/mL).

Cultured recipient PBMCs are collected by centrifugation on day 7 from the start of the culture and adjusted to $4\times10^6$ cells/mL in the medium described above. Newly prepared irradiated donor PBMCs are added to the cultured recipient PBMCs so that the ratio of cell counts would be 2:1, and an inhibitory factor (e.g., for each of anti-CD80 antibodies/anti-CD86 antibodies, final concentration of 5 μg/mL to 10 μg/ml; for belatacept (or abatacept), final concentration of 10 μg/ml to 40 μg/ml) is also added. The cells are cultured for 7 days under the same condition described above (cell density: $4\times10^6$ cells/mL).

(Evaluation of the Ability to Suppress Immune Response)
Induced cells were collected by centrifugation on day 14 from the start of the culture. A mixed lymphocyte test was conducted in accordance with a method already described in a reference (3). A cell suspension is co-cultured in a 37° C. 5% $CO_2$ incubator. The ability to suppress immune responses can be studied by adding 3H-thymidine (10 μl) on day 4 from the start of the co-culture, removing 3H-thymidine in the culture on day 5 from the start of the co-culture (16 to 20 hours after the addition of 3H-thymidine), and measuring the amount of 3H-thymidine incorporation.

Example 9: Quality Control for Cell Formulation

See the descriptions in Examples 1 to 7 for the manufacturing method of a cell formulation. The quality of a cell formulation manufactured in accordance with the Examples is controlled as follows.

Representative examples of quality specification to be met are the following.

TABLE 4

| | | Quality specification of final product | | |
|---|---|---|---|---|
| Item | | Shipping upon conducting a clinical trial Tested item | Testing method | Provisional specification value |
| Confirmation test | Outer appearance | Outer appearance test | Visual inspection | Slightly yellowish white to light yellow cell suspension |
| | Cellular phenotype | Ratio of CD3 positive cells | FCM | ≥50% |
| | | Ratio of CD8 positive CD44 positive cells in CD3 positive cells | FCM | ≥5% |

TABLE 4-continued

| | Quality specification of final product | | |
|---|---|---|---|
| | Ratio of CD4 positive CD44 positive cells in CD3 positive cells | FCM | ≥5% |
| | Ratio of CD4 positive CD25 positive cells in CD3 positive cells | FCM | ≥5% |
| Purity test | Ratio of CD45 positive cells | FCM | ≥95% |
| Safety | Sterility test | Method in Japanese Pharmacopoeia | Growth of microorganism not found |
| | Endotoxin | Method in Japanese Pharmacopoeia | <0.25 EU/ml |
| | Mycoplasma | Method in Japanese Pharmacopoeia | Negative |
| Cell count | Cell count | Hemocytometer | $1 \times 10^8$ to $30 \times 10^8$ cells |
| Viable cell ratio | Viable cell ratio | Trypan-blue | ≥70% |

(Cell Formulation Quality Control Test)

For example, the following tests are conducted to find whether anergic cells produced in accordance with the descriptions in Examples 1 to 7 meet the quality specification for a final product by the method described herein.

Outer Appearance

The outer appearance of anergic cells suspended in saline is visually inspected. A suspension meeting the quality specification should consist of slightly yellowish white to light yellow cells.

Cellular Phenotype and Purity of Anergic Cells

Anergic cells are analyzed through multiple staining using, for example, the following antibodies to find each phenotype by flow cytometry:

CD3: FITC fluorescence labeled anti-human CD3 antibodies (UCHT1; eBioscience #11-0038-42) or Pacific Blue fluorescence labeled anti-human CD3 antibodies (UCHT1; Invitrogen #CD0328)

CD4: PE fluorescence labeled anti-human CD4 antibodies (RPA-T4; eBioscience #25-0049-42)

CD8: APC fluorescence labeled anti-human CD8 antibodies (RPA-T8; eBioscience #17-0088-42)

CD25: PerCP fluorescence labeled anti-human CD25 antibodies (MEM-181; eBioscience #A15802)

CD44: PE-Cy7 fluorescence labeled anti-human CD44 antibodies (IM7; eBioscience #25-0441-82)

CD45: Brilliant Violet fluorescence labeled anti-human CD45 antibodies (HI30; BioLegend #304032)

CD45RA: FITC fluorescence labeled anti-CD45RA antibodies (ALB11; Beckman Coulter A07786) or PE fluorescence labeled anti-CD45RA antibodies (ALB11; Beckman Coulter IM1834U)

CD45RO: ECD fluorescence labeled anti-CD45RO antibodies (UCHL1; Beckman Coulter IM2712U) or PE fluorescence labeled anti-CD45RO antibodies (UCHL1; Beckman Coulter A07787) or APC fluorescence labeled anti-CD45RO antibodies (UCHL1; Bay biosciences 20-0457)

Procedure

Ratio of CD3 positive cells, ratio of CD45 positive cells in viable cells, ratio of CD8 positive CD44 positive cells in CD3 positive cells, ratio of CD4 positive CD44 positive cells in CD3 positive cells, ratio of CD8 positive CD45RA negative cells in CD3 positive cells, ratio of CD8 positive CD45RA negative CD45RO positive cells in CD3 positive cells, ratio of CD4 positive CD45RA negative CD45RO positive cells in CD3 positive cells, and ratio of CD4 positive CD25 positive cells in CD3 positive cells Anergic cells suspended in saline are reacted with the antibody described above and then dead cells are stained using a Zombie NIR Fixable Viability Kit (BioLgened #423106). For cells subjected to multiple fluorescence staining, the ratio of CD3 positive cells in all viable cells is determined in FACS Verse (BD Bioscience).

For anergic cells meeting the quality specification, 50% or more of the cells should be CD3 positive. At the same time, the ratio of CD45 positive cells in viable cells, ratio of CD8 positive CD44 positive cells, ratio of CD4 positive CD44 positive cells, ratio of CD8 positive CD45RA negative cells, ratio of CD8 positive CD45RA negative CD45RO positive cells, ratio of CD4 positive CD45RA negative CD45RO positive cells, and ratio of CD4 positive CD25 positive cells in all live CD3 positive cells are determined based on fluorescence.

For anergic cells meeting the quality specification, 95% or more of viable cells should be CD45 positive, and the cells do not contain a significant amount of impurities such as red blood cells and platelets. Furthermore, anergic cells meeting the quality speciation are cells wherein 5% or more are CD8 positive CD44 positive, 5% or more are CD4 positive CD44 positive cells, 5% or more are CD8 positive CD45RA negative, 5% or more are CD8 positive CD45RA negative CD45RO positive, 5% or more are CD4 positive CD45RA negative CD45RO positive, and 5% or more are CD4 positive CD25 positive cells in the CD3 positive cell population.

Safety

Basically, an experiment is conducted in accordance with the descriptions in the Japanese Pharmacopoeia or a corresponding pharmacopoeia in another country. Exemplary embodiments are detailed hereinafter.

Sterility Testing Method

Anergic cell suspension is lightly centrifuged, and the supernatant thereof is subjected to a sterility test. The direct method, which is a representative sterility test in the Japanese Pharmacopoeia, seeds the supernatant in a soybean/casein/digest medium or liquid thioglycolate medium and cultures the supernatant for 14 days or more at 30 to 35° C. or 20 to 25° C., respectively. The culture is then observed several times during the culture period. Membrane filtration, which is another representative sterility test, dilutes supernatant with a sterile diluent (e.g., 1 g/L of meat or casein peptone solution (pH of 7.1±0.2)), and transfers the diluted supernatant onto a membrane filter for filtration. The membrane filter is then placed in each of the two types of medium described above and cultured for 14 days or more. In a product meeting the quality specification, proliferation of microorganisms is not detected from visual inspection in the medium during the culture period and the final day.

Endotoxin Testing

An anergic cell suspension is diluted as appropriate with saline and adjusted to a pH of 6.0 to 8.0. The endotoxin concentration in a sample is then quantitatively determined by mixing the suspension with a lysate reagent and using gel formation of the lysate reagent as an indicator (gelation method), or using the change in turbidity in the gelling process the lysate reagent as an indicator (turbidimetry), or using coloring due to hydrolysis of a synthesis substrate as an indicator (colorimetry). A preliminary test for confirming the displayed sensitivity of the lysate reagent is performed as needed. For a product meeting the quality specification, the endotoxin concentration must be less than 0.25 EU/mL.

Mycoplasma Test

A culture or anergic cell suspension is lightly centrifuged, and the supernatant thereof is subjected to a mycoplasma test. A culture method, which is a representative mycoplasma test in the Japanese Pharmacopoeia, seeds a sample in an agar plate and cultures the sample for 14 days in nitrogen gas comprising 5 to 10% carbon dioxide gas under a suitable humidity at 35 to 37° C., or seeds a sample in a container comprising a liquid medium and cultures the sample at 35 to 37° C., harvests an aliquot from the liquid culture when a change in the color tone of the liquid medium is observed or at a certain interval from the start of the culture, and seeds the aliquot in a new agar plate to continue culturing. The presence of a colony of mycoplasma is investigated in all agar plates with a microscope at a 100× magnification or greater on day 7 and day 14. The DNA staining method using an indicator cell, which is another representative mycoplasma test, typically uses an indicator cell Vero cell and a designated mycoplasma strain. This method seeds an indicator cell in a culture dish or the like with a cover glass placed therein and allows the cell to proliferate for 1 day at 35 to 38° C. in air containing 5% carbon dioxide gas. A sample (culture or supernatant) is then added, and the culture is continued for 3 to 6 days under the same condition. After immobilizing the cultured cells on the cover glass, DNA fluorescent staining is performed with a stain such as bisbenzimide. The cells are observed with a fluorescence microscope (magnification of 400× to 600× or greater), and a negative (unseeded) control and a mycoplasma positive control are compared therewith. If, while doing so, 0.5% or more of the cells have a minute extranuclear fluorescent spot surrounding the cell nucleus, the cells are deemed mycoplasma positive. A product meeting the quality specification should be mycoplasma negative.

Cell Count

The cell count of anergic cells suspended in saline is taken under a microscope using a hemocytometer or with an automatic cell counter. An anergic cell count that is suitable for administration and meets the quality specification is $1 \times 10^8$ to $30 \times 10^8$ cells (e.g., in 100 mL of saline). If the cell count is below this range, cells should be added as appropriate.

Viable Cell Ratio

Anergic cells suspended in saline are mixed with 0.3 to 0.5% trypan-blue stain (e.g., catalog #35525-02, Nacalai Tesque), and the viable cell count is taken under a microscope using a hemocytometer or with an automatic cell counter. In a product meeting the quality specification, 70% or more of the cells should be viable cells.

Discussion

In view of the above results, the composition of the present disclosure is 1) a population of immune suppressed cells mainly of CD44 positive CD8 positive T cells and CD44 positive CD4 positive T cells, and the performance thereof is strongly exerted by being a mixture.
2) It is suggested that this cell population also contains FoxP3 positive reg T cells, but the suppression ability of such reg T cells is also enhanced in a culture system inducing anergy with antigen stimulation in the presence of anti-CD80/86 antibodies. The suppression ability thereof is more strongly exerted in the presence of a CD44 positive CD8 positive cell or CD44 positive CD4 positive cell.
3) It was proven that one of the mechanisms of immunosuppression is through an anergic CD8 positive cell and anergic CD4 positive cell, which have been reacted with an antigen in the presence of anti-CD80/86 and selected and become antigen specific, recognizing and covering an antigen more quickly than a naïve cell. These are very important findings that were not elucidated in conventional rejection suppression experiments.

These findings can be an important check point in the quality control of a cell formulation for rejection suppression.

The specification of the final product shown in Table 4 is a representative example. The baseline value for the cellular phenotype or the like can be appropriately changed. Modified examples thereof include the examples described in Table 3.

MENTIONED REFERENCES

The following Mentioned References were referenced as a fundamental technology in the Examples and the like. It is not acknowledged that these references constitute prior art to the present disclosure. The content thereof is incorporated by reference.

1. Bashuda H, Kimikawa M, Seino K, Kato Y, Ono F, Shimizu A, et al. Renal allograft rejection is prevented by adoptive transfer of anergic T cells in nonhuman primates. The Journal of clinical investigation. 2005; 115 (7): 1896-902.

2. Bashuda H, Shimizu A, Uchiyama M, Okumura K. Prolongation of renal allograft survival by anergic cells: advantages and limitations. Clin Transplant. 2010; 24 Suppl 22:6-10.
3. Luo Z, Gotoh M, Grochowiecki T, Tanaka T, Kimura F, Kawashima H, et al. Anergic T cells generated in vitro suppress rejection response to islet allografts. Transplantation. 2000; 69 (10): 2144-8.
4. Miyao T, Floess S, Setoguchi R, Luche H, Fehling H J, Waldmann H, et al. Plasticity of Foxp3 (+) T cells reflects promiscuous Foxp3 expression in conventional T cells but not reprogramming of regulatory T cells. Immunity. 2012; 36 (2): 262-75.
5. Davies J K, Barbon C M, Voskertchian A, Nadler L M, Guinan E C. Ex vivo alloanergization with belatacept: a strategy to selectively modulate alloresponses after transplantation. Cell transplantation. 2012; 21 (9): 2047-61.
6. Davies J K, Gribben J G, Brennan L L, Yuk D, Nadler L M, Guinan E C. Outcome of alloanergized haploidentical bone marrow transplantation after ex vivo costimulatory blockade: results of 2 phase 1 studies. Blood. 2008; 112 (6): 2232-41.
7. Davies J K, Nadler L M, Guinan E C. Expansion of allospecific regulatory T cells after anergized, mismatched bone marrow transplantation. Science translational medicine. 2009; 1 (1): 1ra3.
8. Davies J K, Yuk D, Nadler L M, Guinan E C. Induction of alloanergy in human donor T cells without loss of pathogen or tumor immunity. Transplantation. 2008; 86 (6): 854-64.

[Note]

As disclosed above, the present disclosure is exemplified by the use of its preferred embodiments. However, it is understood that the scope of the present disclosure should be interpreted based solely on the Claims. It is also understood that any patent, any patent application, and any other references cited herein should be incorporated herein by reference in the same manner as the contents are specifically described herein. The present application claims priority to Japanese Patent Application No. 2018-119001 (filed on Jun. 22, 2018). It [is understood that the content thereof (can be the entire document) is incorporated herein by reference. Further, a part of or the entire content of Japanese Patent Application No. 2018-118996 and Japanese Patent Application No. 2018-119003 (both filed on Jun. 22, 2018) and international applications claiming priority thereto is incorporated herein by reference.

INDUSTRIAL APPLICABILITY

The present disclosure provides a pharmaceutical composition comprising a cell having immune tolerance induced that is specific to a specific antigen. A technology that can be utilized in industries (pharmaceutical) related to formulations or the like based on such a technology is provided.

The invention claimed is:

1. A method of treating or preventing a disease, disorder, or condition in a subject caused by an antigen derived from the subject or an antigen that is not derived from the subject, comprising providing a CD4 positive anergic T cell and a CD8 positive anergic T cell, confirming that the CD4 positive anergic T cell and the CD8 positive anergic T cell are both CD44 positive; optionally removing CD8 positive CD44 negative cells or CD4 positive CD44 negative cells; administering to the subject a composition comprising an effective amount of the resultant CD4 positive anergic T cell and the resultant CD8 positive anergic T cell, wherein the CD4 positive anergic T cell and the CD8 positive anergic T cell are both CD44 positive.

2. The method of claim 1, wherein the CD4 positive anergic T cell and the CD8 positive anergic T cell are induced by an inhibitory factor that can inhibit an interaction between CD80 and/or CD86 and CD28.

3. The method of claim 2, wherein the inhibitory factor is selected from the group consisting of a small molecule, a protein, a nucleic acid, a lipid, a saccharide, and a combination thereof.

4. The method of claim 3, wherein the protein is an antibody or a variant thereof, or a cell surface molecule or a variant thereof.

5. The method of claim 4, wherein the variant of the antibody is an antigen binding fragment.

6. The method of claim 4, wherein the variant of the cell surface molecule is a fusion protein.

7. The method of claim 2, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.

8. The method of claim 1, further comprising administering a regulatory T cell.

9. The method of claim 8, wherein the regulatory T cell is FOXP3 positive CD4 positive CD25 positive.

10. The method according to claim 1, wherein the disease, disorder, or condition comprises graft rejection.

11. The method according to claim 10, wherein the treatment is achieved by antigen specific immune tolerance or immunosuppression.

12. The method according to claim 1, wherein the composition comprises CD3 positive cells, and wherein the step of confirming further comprises confirming that:
 (i) the CD8 positive CD44 positive cells comprise greater than or equal to 5% of the total CD3 positive cells, and
 (ii) the CD4 positive CD44 positive cells comprise greater than or equal to 5% of the total CD3 positive cells.

* * * * *

UNITED STATES PATENT AND TRADEMARK OFFICE
CERTIFICATE OF CORRECTION

PATENT NO. : 12,397,054 B2
APPLICATION NO. : 17/254094
DATED : August 26, 2025
INVENTOR(S) : Koichiro Uchida et al.

Page 1 of 1

It is certified that error appears in the above-identified patent and that said Letters Patent is hereby corrected as shown below:

On the Title Page

<u>Abstract (57), Lines 2 and 3:</u>
"immune present suppression. The disclosure provides pharmaceutical"
Should read:
--immune suppression. The present disclosure provides a pharmaceutical--.

Signed and Sealed this
Twenty-eighth Day of October, 2025

John A. Squires
*Director of the United States Patent and Trademark Office*